US012758211B2

(12) United States Patent
Hayashi et al.

(10) Patent No.: US 12,758,211 B2
(45) Date of Patent: Oct. 13, 2026

(54) TRACTION TOOL, AND TRACTION METHOD FOR SUTURE THREAD AND SUTURING METHOD

(71) Applicant: Olympus Corporation, Tokyo (JP)

(72) Inventors: Yuta Hayashi, Tokyo (JP); Masatoshi Tonomura, Tokyo (JP); Kunihide Kaji, Tokyo (JP)

(73) Assignee: Olympus Corporation, Tokyo (JP)

( * ) Notice: Subject to any disclaimer, the term of this patent is extended or adjusted under 35 U.S.C. 154(b) by 459 days.

(21) Appl. No.: 18/178,195

(22) Filed: Mar. 3, 2023

(65) Prior Publication Data

US 2023/0200804 A1 Jun. 29, 2023

Related U.S. Application Data

(63) Continuation of application No. PCT/JP2020/038566, filed on Oct. 13, 2020.

(51) Int. Cl.
*A61B 17/04* (2006.01)

(52) U.S. Cl.
CPC .. *A61B 17/0469* (2013.01); *A61B 2017/0496* (2013.01)

(58) Field of Classification Search
CPC ............ A61B 17/0469; A61B 17/0482; A61B 17/062; A61B 2017/0496; A61B 2017/0608; A61B 2017/06176; A61B 2017/0034; A61B 2017/00557
See application file for complete search history.

(56) References Cited

U.S. PATENT DOCUMENTS 4,737,142 A * 4/1988 Heckele ................. A61B 1/015 600/116
4,784,133 A * 11/1988 Mackin .................. A61B 18/24 606/7
4,787,899 A * 11/1988 Lazarus .................... A61F 2/82 623/1.14
5,545,171 A * 8/1996 Sharkey ............. A61B 17/0469 606/139
5,716,368 A * 2/1998 de la Torre ........ A61B 17/0469 606/139

(Continued)

FOREIGN PATENT DOCUMENTS

CN 108670330 10/2018
JP 2002306496 A 10/2002

OTHER PUBLICATIONS

Kalanovic, D., Buess, G., Kayser, J. et al. The Tübingen balloon. Surg Endosc 14, 382-387 (2000). (Year: 2000).*

(Continued)

*Primary Examiner* — Tan-Uyen T Ho
*Assistant Examiner* — Osama Nemer
(74) *Attorney, Agent, or Firm* — Schwegman Lundberg & Woessner, P.A.

(57) ABSTRACT

A traction tool for performing traction of a suture thread under a flexible endoscope is provided. The tool includes a shaft, a first holder which is provided at a distal end of the shaft and is configured to hold the suture thread or a suture needle attached to the suture thread, and a second holder which is provided closer to a proximal end side of the shaft than the first holder and to which the suture thread is hooked. The second holder is expandable in a radial direction of the shaft.

12 Claims, 22 Drawing Sheets

(56) References Cited

U.S. PATENT DOCUMENTS

| | | | | |
|---|---|---|---|---|
| 5,816,258 | A * | 10/1998 | Jervis | A61B 17/0483 606/139 |
| 9,498,604 | B2 * | 11/2016 | Dubrul | A61B 17/12022 |
| 2002/0010475 | A1 * | 1/2002 | Lui | A61N 1/056 606/108 |
| 2002/0156497 | A1 | 10/2002 | Nagase et al. | |
| 2005/0182427 | A1 * | 8/2005 | Manzo | A61B 17/0469 606/144 |
| 2009/0306685 | A1 * | 12/2009 | Fill | A61B 17/12131 606/148 |
| 2012/0016383 | A1 * | 1/2012 | Sauer | A61B 17/0483 606/144 |
| 2014/0121680 | A1 | 5/2014 | Uchida et al. | |
| 2018/0042602 | A1 | 2/2018 | Mitelberg et al. | |

OTHER PUBLICATIONS

Hirohito Mori et al., “Balloon-Armed Mechanical Counter Traction and Double-Armed Bar Suturing Systems for Pure Endoscopic Full-Thickness Resection”, Aug. 2014, Gastroenterology, vol. 147, Issue 2, pp. 278-280.e1 (Year: 2014).*

“International Application Serial No. PCT/JP2020/038566, International Search Report dated Dec. 1, 2020”, (Dec. 1, 2020), 4 pgs.

“Chinese Application No. 202080103856.5, Office Action dated Mar. 19, 2025”, w English Translation, (Mar. 19, 2025), 18 pgs.

* cited by examiner

TRACTION TOOL, AND TRACTION METHOD FOR SUTURE THREAD AND SUTURING METHOD

CLAIM FOR PRIORITY

CROSS REFERENCE TO RELATED APPLICATIONS

This application is a continuation application based on International Patent Application No. PCT/JP2020/038566 filed on Oct. 13, 2020, the contents of the PCT international application is incorporated herein by reference.

TECHNICAL FIELD

The present disclosure relates to a traction tool, a traction method for a suture thread, and a suturing method.

BACKGROUND ART

In the related art, a procedure of suturing a wound inside a luminal organ such as the digestive tract under observation using an endoscope has been performed. In such a procedure, a tool such as an endoscopic needle holder allowing needle work to be performed by grasping a suture needle has been used.

United States Patent Application, Publication No. 2018/042602 discloses an endoscopic suturing tool. The suturing tool disclosed in United States Patent Application, Publication No. 2018/042602 pulls a tissue and pierces the pulled-out tissue by a suture needle. The endoscopic suturing tool hooks a suture thread to a tip of the suture needle which has penetrated the tissue and sutures the tissue by returning the suture needle to an original position.

SUMMARY OF INVENTION

Technical Problem

In consideration of the foregoing circumstances, an object of the present disclosure is to provide a traction tool, a traction method for a suture thread, and a suturing method capable of sufficiently stitching a wound by pulling a suture thread attached to a suture needle in suturing work inside a confined hollow organ.

Solution to Problem

In order to resolve the foregoing problems, the present disclosure proposes the following means.

A traction tool according to a first aspect of the present disclosure performs traction of a suture thread under a flexible endoscope. The traction tool includes a shaft. a first holder which is provided at a distal end of the shaft and is configured to hold the suture thread or a suture needle attached to the suture thread, and a second holder which is provided closer to a proximal end side of the shaft than the first holder and to which the suture thread is capable of being hooked. The second holder is expandable in a radial direction of the shaft.

A traction method for a suture thread according to a second aspect of the present disclosure uses the traction tool described above. The traction method for a suture thread includes performing traction of the suture thread by winding the suture thread around the second holder extended in the radial direction in a state in which the suture thread or a suture needle fixed to the suture thread is held by the first holder.

A suturing method according to the third aspect of the present disclosure closes a wound formed in a lumen wall of a hollow organ using a traction tool including a shaft, a first holder which is provided at a distal end of the shaft and is configured to hold a suture thread or a suture needle attached to the suture thread, and a second holder which is provided closer to a proximal end side of the shaft than the first holder, to which the suture thread is capable of being hooked, and which is configured to be expandable in a radial direction of the shaft. The suturing method includes a first step of hooking the suture thread to a first edge portion of the wound; a second step of hooking the suture thread to a second edge portion of the wound, the suture thread extending from the first edge portion, and the second edge portion being located at a position facing the first edge portion with the wound interposed therebetween; and a third step of winding a second portion of the suture thread around the shaft while the second portion is hooked to the second holder in a state that the suture needle or a first portion of the suture thread extending from the second edge portion is held, the second portion extending between the suture needle or the first portion and the second edge portion.

DESCRIPTION OF EMBODIMENTS

First Embodiment

Figure 1:
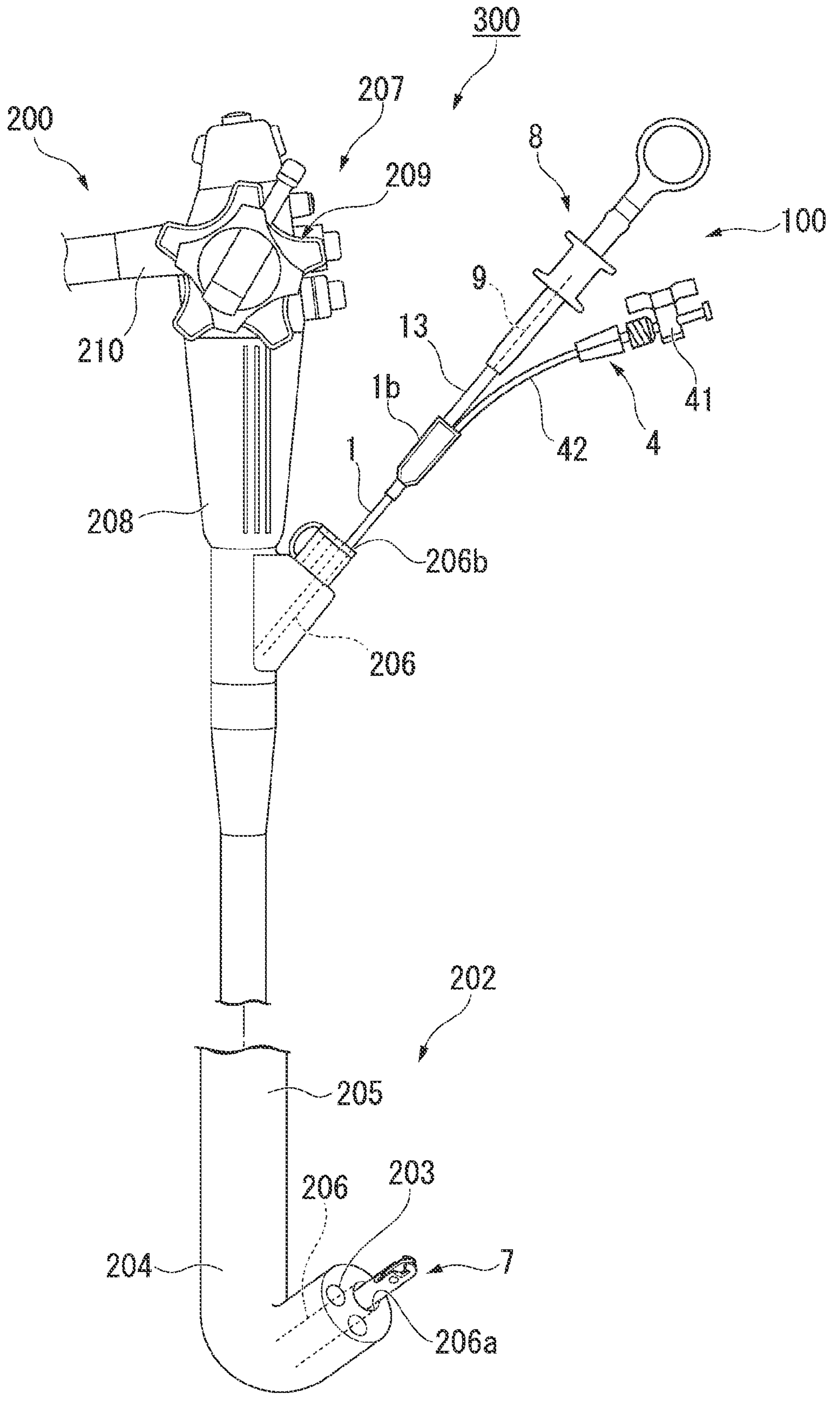
FIG. 1 is a general view of a treatment system according to a first embodiment.

A treatment system 300 according to a first embodiment of the present disclosure will be described with reference to FIGS. 1 to 18. FIG. 1 is a general view of the treatment system 300 according to the present embodiment.

[Treatment System 300]

As illustrated in FIG. 1, the treatment system 300 includes a flexible endoscope 200 and a traction tool 100. The traction tool 100 is used so as to be inserted into the flexible endoscope 200.

[Flexible Endoscope 200]

As illustrated in FIG. 1, the flexible endoscope 200 includes an insertion portion 202 inserted into a human body from a distal end thereof, and an operation portion 207 attached to a proximal end of the insertion portion 202.

The insertion portion 202 has an image capturing portion 203, a bent portion 204, and a flexible portion 205. From a distal end of the insertion portion 202, the image capturing portion 203, the bent portion 204, and the flexible portion 205 are each arranged in this order. A channel 206 for inserting the traction tool 100 is provided inside the insertion portion 202. A distal end opening portion 206*a* of the channel 206 is provided at the distal end of the insertion portion 202.

For example, the image capturing portion 203 includes an image capturing element such as a CCD or CMOS, and configured to capture an image of a part of a treatment target. The image capturing portion 203 configured to capture an image of a grasper 7 of the traction tool 100 in a state in which the traction tool 100 protrudes from the distal end opening portion 206*a* of the channel 206.

The bent portion 204 is bent in accordance with an operation of the operation portion 207 by an operator. The flexible portion 205 is a tubular part having flexibility.

The operation portion 207 is connected to the flexible portion 205. The operation portion 207 has a grip 208, an input portion 209, a proximal end opening portion 206*b* of the channel 206, and a universal cord 210. The grip 208 is a part grasped by an operator. The input portion 209 receives an operational input for bending operation of the bent portion 204. The universal cord 210 outputs an image captured by the image capturing portion 203 to the outside. The universal cord 210 is connected to a display device such as a liquid crystal display via an image processing device including a processor and the like.

[Traction Tool 100]

Figure 2:
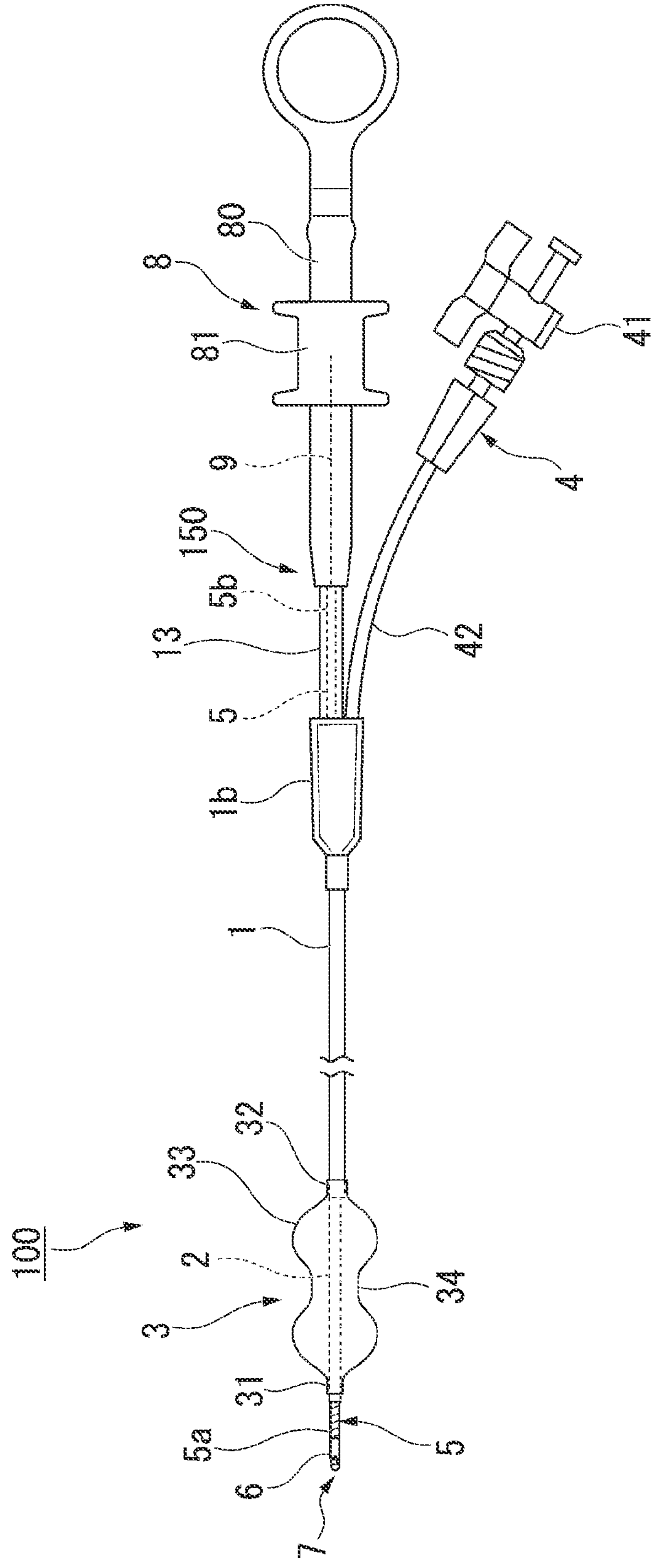
FIG. 2 is a general view illustrating a traction tool in the treatment system.

FIG. 2 is a general view illustrating the traction tool 100. The traction tool 100 includes a proximal shaft 1, a distal shaft 2, a balloon (second holder) 3, a hub 4, and a needle holder 150.

Figure 3:
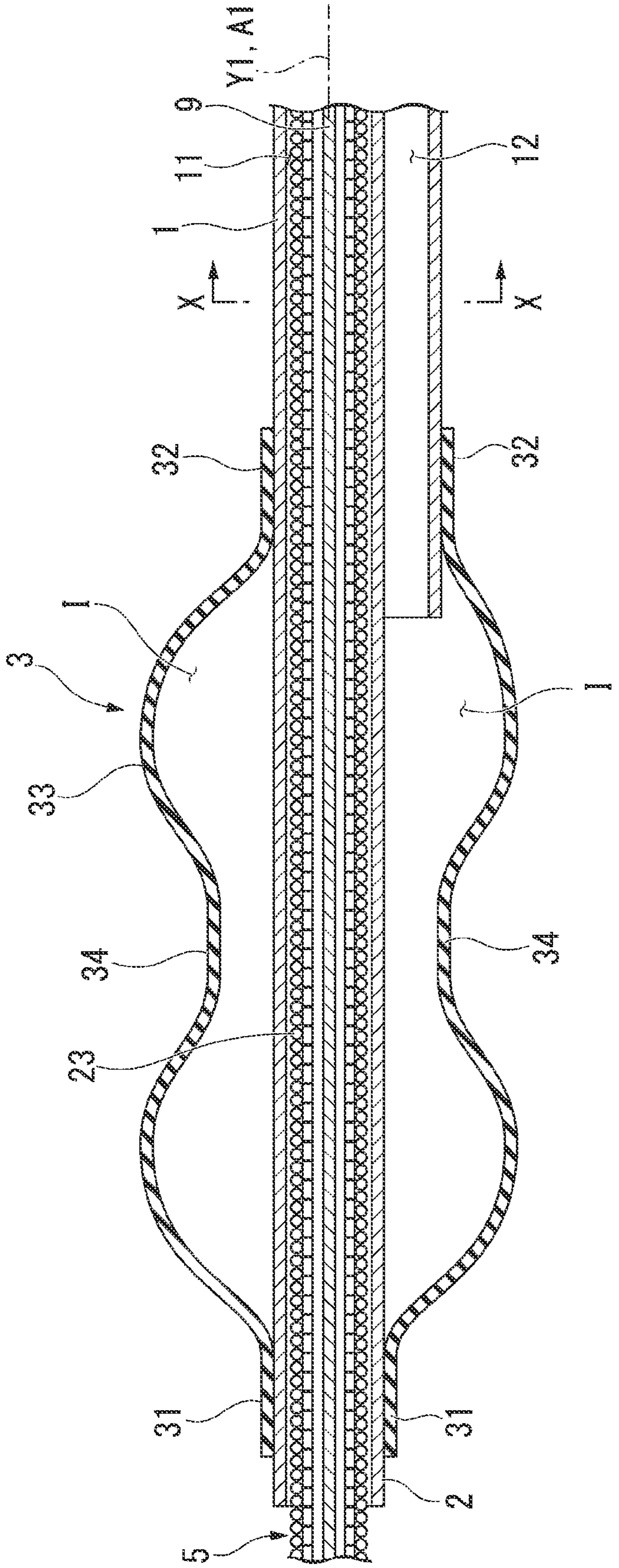
FIG. 3 is a cross-sectional view of a distal end portion of the traction tool.

FIG. 3 is a cross-sectional view of a distal end portion of the traction tool 100.

The proximal shaft 1 is an elongated member endoscopically inserted into a body cavity. The proximal shaft 1 is insertable into the channel 206 of the flexible endoscope 200. The proximal shaft 1 has flexibility.

Figure 4:
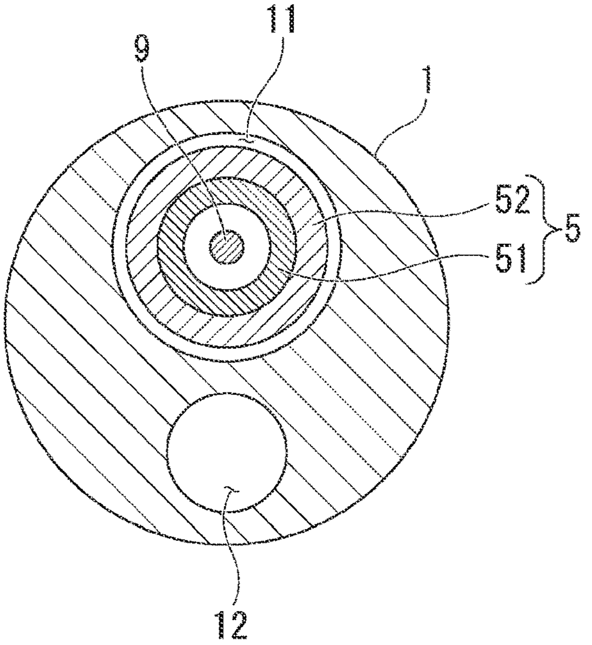
FIG. 4 is a cross-sectional view along line X-X indicated in FIG. 3.

FIG. 4 is a cross-sectional view along line X-X indicated in FIG. 3.

The proximal shaft 1 has a first lumen 11 and a second lumen 12. The first lumen 11 and the second lumen 12 penetrate the proximal shaft 1 in a longitudinal direction. The first lumen 11 and the second lumen 12 are disposed parallel to each other (biaxial type). For example, plurality of the first lumens 11 may be disposed in a manner of surrounding an outer circumferential portion of the second lumen 12 (coaxial type).

On a distal side from the proximal shaft 1, the distal shaft 2 extends from an end surface on the distal side of the proximal shaft 1. An outer diameter of the distal shaft 2 is smaller than an outer diameter of the proximal shaft 1.

The proximal shaft 1 has a proximal end portion 1*b* having a larger outer diameter than other parts on the proximal end side. The proximal end portion 1*b* cannot be inserted into the channel 206 of the flexible endoscope 200. In addition, the proximal shaft 1 has a coupling member 13 coupling the proximal end portion 1*b* and an operation portion 8 of the needle holder 150 to each other. The coupling member 13 is formed to have a cylinder shape.

The distal shaft 2 is a shaft-shaped member endoscopically inserted into a body cavity. The distal shaft 2 extends in the longitudinal direction of the proximal shaft 1. The distal shaft 2 has a third lumen 23. The third lumen 23 penetrates the distal shaft 2 in the longitudinal direction. The third lumen 23 communicates with the first lumen 11 of the proximal shaft 1. As illustrated in FIGS. 3 and 4, a sheath 5 of the needle holder 150 is inserted through the first lumen 11 and the third lumen 23.

The balloon (second holder) 3 is a thin-walled cylindrical member. For example, the balloon 3 is formed of an elastic material such as a natural rubber, or the like. The balloon 3 has a first connection portion 31, a second connection portion 32, and a balloon main body 33. An internal space I of the balloon main body 33 communicates with the second lumen 12 of the proximal shaft 1. An opening communicating with the external space is not formed in the internal space I of the balloon main body 33 except for the second lumen 12. In other word, the internal space I of the balloon main body 33 communicates with the external space of the balloon 3 via only the second lumen 12. Accordingly, a fluid can be supplied to the balloon 3 via the second lumen 12. If a fluid is supplied to the internal space I, the balloon 3 expands (is increased in diameter) in a radial direction of the distal shaft 2. A fluid may be a liquid or a gas. Examples of a fluid include a contrast medium, helium gas, a physiological salt solution, carbon dioxide ($CO_2$) gas, oxygen ($O_2$) gas, nitrogen ($N_2$) gas, and air.

In the following description, a state in which the balloon 3 is not inflated will be defined as "a natural state" of the balloon 3. A state, as a result of inflation of the balloon 3, in which at least a part has expanded in diameter compared to the natural state will be defined as "a diameter-expanded state" of the balloon 3.

The first connection portion 31 has a tubular shape. The first connection portion 31 is formed in an end portion on the distal side of the balloon 3. The first connection portion 31 is liquid-tightly attached to an outer circumferential surface of the distal shaft 2 in a state in which the first connection portion 31 covers an end portion on the distal side of the distal shaft 2.

A means for bonding the first connection portion 31 and the distal shaft 2 to each other is not particularly limited as long as they are liquid-tightly attached to each other. For example, the means for bonding the first connection portion 31 and the distal shaft 2 to each other may be an adhesive or heat fusion.

The second connection portion 32 has a tubular shape. The second connection portion 32 is formed in an end portion on a proximal side in the balloon 3. The second connection portion 32 is liquid-tightly attached to an outer circumferential surface of the proximal shaft 1 in a state in which an end portion on the distal side of the proximal shaft 1 is covered.

A means for bonding the second connection portion 32 and the proximal shaft 1 to each other is not particularly limited as long as they are liquid-tightly attached to each other. For example, the means for bonding the second connection portion 32 and the distal shaft 2 may be an adhesive or heat fusion.

The balloon main body 33 is positioned between the first connection portion 31 and the second connection portion 32. That is, the balloon main body 33 is interposed between the first connection portion 31 and the second connection portion 32. The balloon main body 33 surrounds at least a part of the distal shaft 2. If the balloon 3 is inflated, an inner circumferential surface of the balloon main body 33 is separated from the outer circumferential surface of the distal shaft 2.

The balloon main body 33 preferably has a recessed portion 34 at an intermediate portion in the longitudinal direction of the balloon main body 33. The recessed portion 34 has an outer diameter smaller than those of other parts in the balloon main body 33 in the diameter-expanded state. The balloon main body 33 may not have the recessed portion 34.

Figure 5:
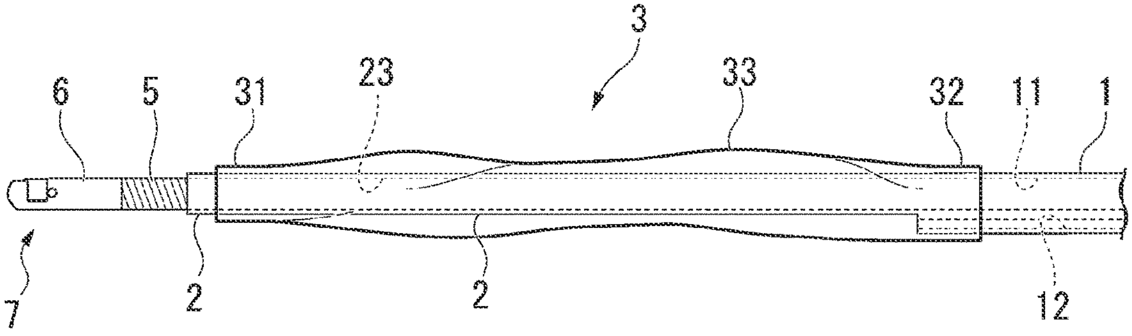
FIG. 5 is a view illustrating a balloon in a natural state.

FIG. 5 is a view illustrating the balloon 3 in the natural state. In a state in which a fluid is not supplied to the internal space I of the balloon main body 33, the balloon main body 33 is disposed in a form of being wound along the outer circumferential surface of the distal shaft 2. In a state in which the balloon main body 33 is wound around the outer circumferential surface of the distal shaft 2, the outer diameter of the balloon main body 33 is substantially equivalent to the outer diameter of the proximal shaft 1. For this reason, in a state in which a fluid is not introduced into the balloon main body 33, the distal shaft 2 can be inserted through the channel 206 of the flexible endoscope 200.

Figure 6:
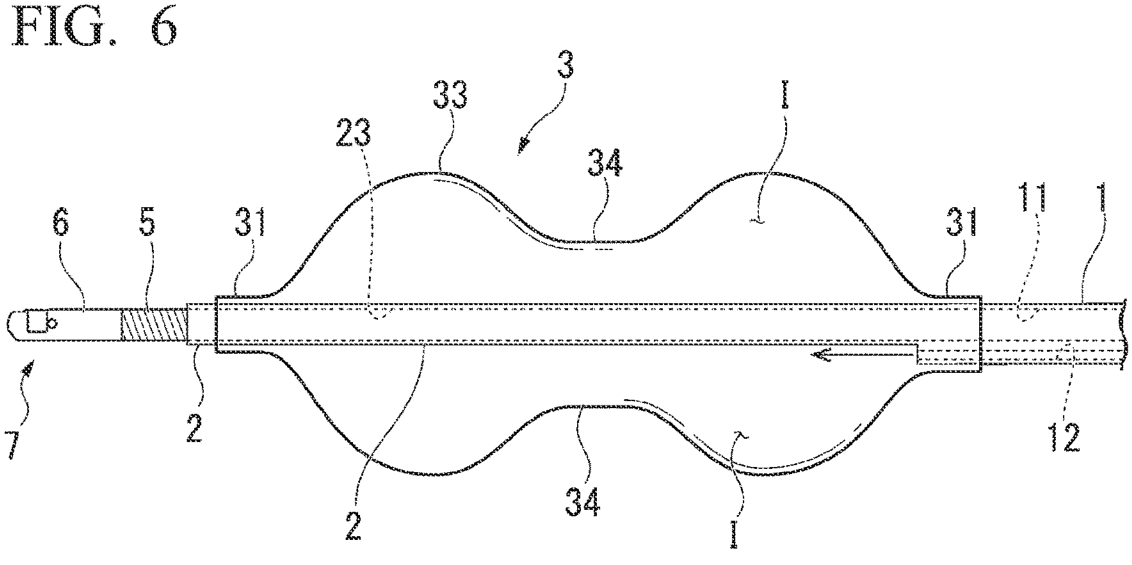
FIG. 6 is a view illustrating the balloon in a diameter-expanded state.

FIG. 6 is a view illustrating the balloon 3 in the diameter-expanded state. If a fluid is supplied from the second lumen 12 to the internal space I, the fluid is confined in the internal space I, and the balloon main body 33 is inflated.

The hub 4 is a valve for allowing a fluid to pass therethrough. A fluid is supplied from a fluid supply device (not illustrated) to the hub 4. For example, the fluid supply device is an inflator or the like and can adjust a pressure of a supplied fluid. The fluid is pressurized by the fluid supply device so as to inflate the balloon 3.

A stop cock 41 is provided on an end portion on a proximal side of the hub 4. The fluid supply device is configured to be connectable to the hub 4 through the stop cock 41. The stop cock 41 opens and closes a flow channel for a fluid.

A tube 42 is connected to an end portion on a distal side of the hub 4. A fluid can flow in the tube 42. The proximal shaft 1 is connected to an end portion on the distal side of the tube 42. An internal space of the tube 42 communicates with the second lumen 12 of the proximal shaft 1. A fluid supplied from the hub 4 flows into the second lumen 12.

As illustrated in FIG. 2, the needle holder 150 includes the sheath 5, a hard portion 6, a grasp portion (first holder) 7, the operation portion 8, and an operation wire 9 for operating the grasper 7.

The sheath 5 is an elongated member having flexibility and extending from a distal end **5*a* to a proximal end 5*b*. As illustrated in FIG. 2, the hard portion 6 is provided at the distal end 5*a* of the sheath 5. The grasper 7 is provided on the hard portion 6. The operation portion 8 is provided at a proximal end 5*b* of the sheath 5. The sheath 5 is inserted into the coupling member 13, the first lumen 11, and the third lumen 23. The sheath 5 can rotate about a longitudinal axis Y1 of the sheath 5 with respect to the coupling member 13, the first lumen 11, and the third lumen 23**.

As illustrated in FIG. 1, in a state that the distal shaft 2 into which the sheath 5 is inserted is inserted into the channel 206, the grasper 7 is projectable from and retractable in the distal end opening portion **206*a* of the channel 206. The grasper 7 can enter the range of an image-capturing visual field of the image capturing portion 203 of the flexible endoscope 200 and an image thereof is captured by the image capturing portion 203**.

Figure 7:
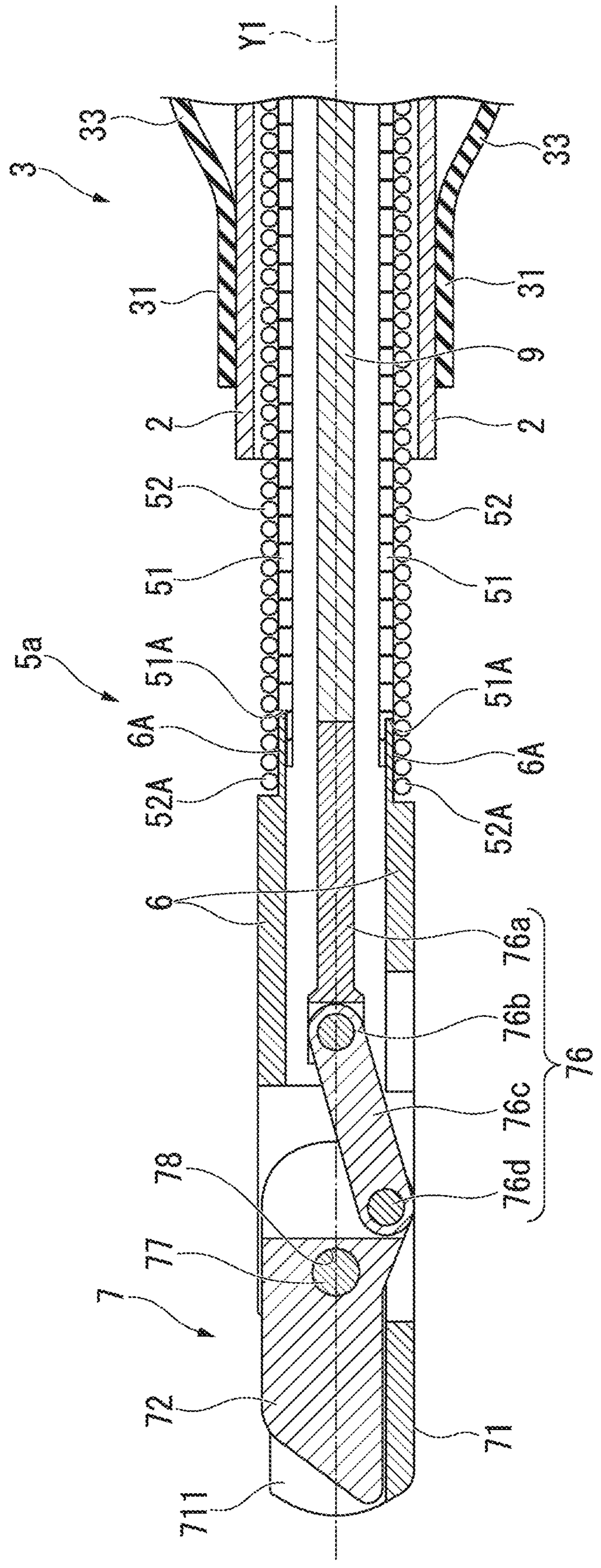
FIG. 7 is a cross-sectional view of a distal end of a sheath in the traction tool.

FIG. 7 is a cross-sectional view of the distal end **5*a* of the sheath 5. The sheath 5 has a first coil sheath 51 through which the operation wire 9 is inserted, and a second coil sheath 52 through which the first coil sheath 51** is inserted.

The first coil sheath 51 is a so-called single-strand coil sheath formed by tightly winding one metal strand wire into a loop shape. The first coil sheath 51 has a compressive resistance with respect to the operation wire 9 which has been inserted therethrough and suitably transmits an opening/closing operation of the grasper 7 via the operation portion 8 to the grasper 7. The first coil sheath 51 is not limited to a coil sheath and may be a resin tube such as a PEEK having an excellent compressive resistance.

The second coil sheath 52 is a so-called multi-strand coil sheath formed by arranging a plurality of metal strand wires in the radial direction and tightly winding them into a loop shape. An operation rotating the hard portion 6 is suitably transmitted to the hard portion 6 by the second coil sheath 52.

As illustrated in FIG. 7, the first coil sheath 51 is formed of a metal strand wire in which a transverse section of the metal strand wire has a rectangular shape. The second coil sheath 52 is formed of a metal strand wire in which a transverse section of the metal strand wire has a circular shape. The shapes of the transverse sections of the metal strand wires in the first coil sheath 51 and the second coil sheath 52 are not limited to these and may be suitably selected in accordance with a design value or the like of the sheath 5.

Figure 8:
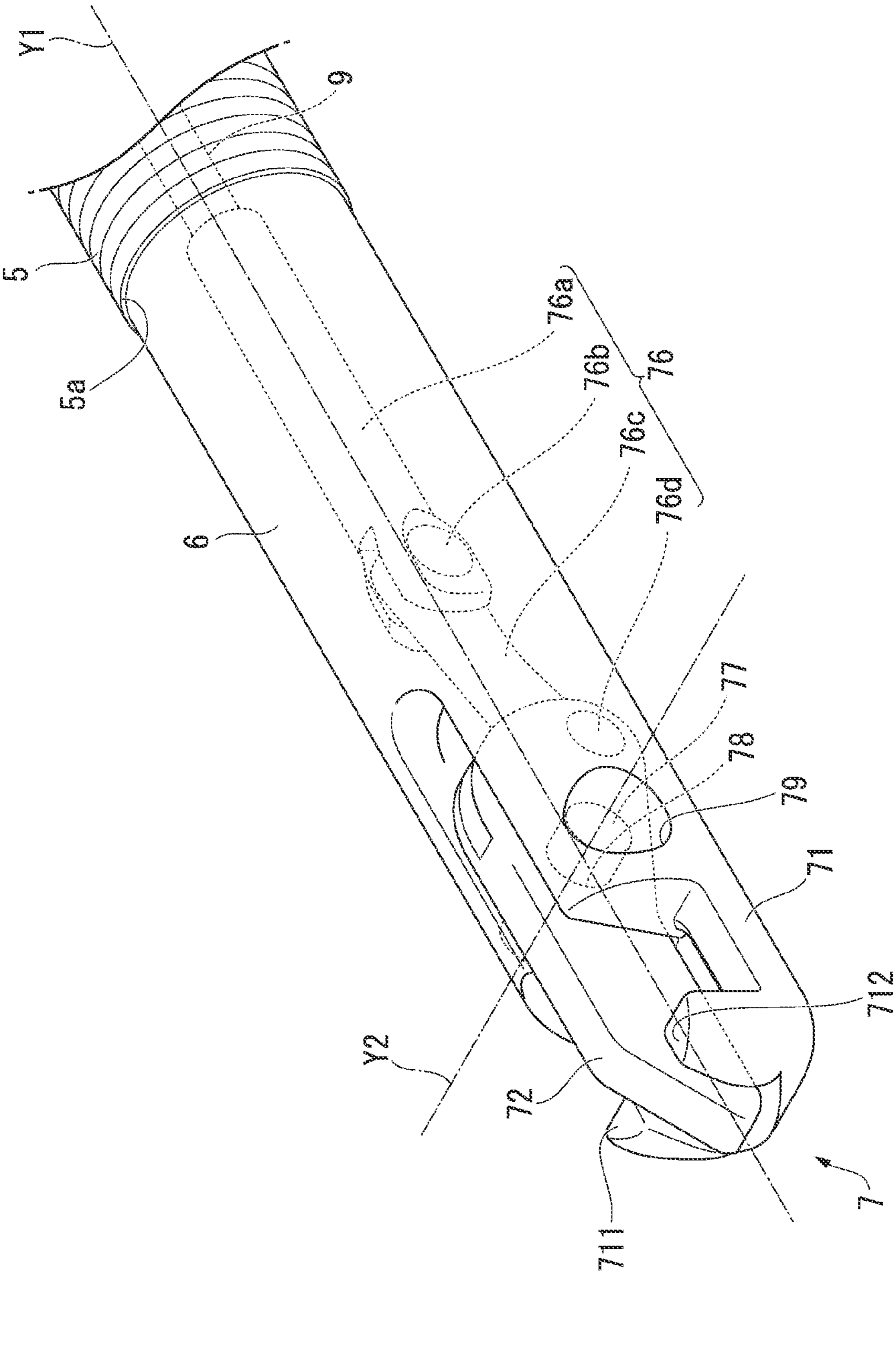
FIG. 8 is a perspective view illustrating a hard portion and a grasp portion in the traction tool.

FIG. 8 is a perspective view illustrating the hard portion 6 and the grasper 7.

The hard portion 6 is formed to have substantially a cylindrical shape. The hard portion 6 is formed of a hard material such as a stainless steel material (SUS).

The hard portion 6 is provided at a distal end of the sheath 5. As illustrated in FIG. 7, a distal end 51A of the first coil sheath 51 is fixed to a proximal end of the hard portion 6 by laser welding, brazing, or the like.

The proximal end side of the hard portion 6 is formed to have a tubular shape and includes an outer surface 6A connected and fixed to the second coil sheath 52 on an outer surface thereof. The outer surface 6A on the proximal end side of the hard portion 6 is fixed to the second coil sheath 52 by laser welding, brazing, or the like.

A distal end 52A of the second coil sheath 52 fixed to the outer surface 6A of the hard portion 6 is unrotatable around an axis with respect to the hard portion 6 and is immovable in an axial direction with respect to the first coil sheath 51.

A connection form between the hard portion 6 and the sheath 5 is not limited to that described above. For example, a constitution in which the second coil sheath 52 is fixed to an outer surface and the first coil sheath 51 is fixed to an inner surface in the proximal end side of the hard portion 6 formed in a cylindncal shape may be adopted. In addition, the shape of a part where the sheath 5 is fixed in the hard portion 6 may not have a tubular shape.

As illustrated in FIGS. 7 and 8, the grasp portion (first holder) 7 has a first grasp member 71, a second grasp member 72, and a link mechanism 76. The first grasp member 71 and the second grasp member 72 are constituted to be able to perform an opening/closing operation. The grasper 7 illustrated in FIG. 7 is in a closed state in which the first grasp member 71 and the second grasp member 72 are closed.

The first grasp member 71 is a part of the distal end portion of the hard portion 6. The first grasp member 71 extends along the longitudinal axis Y1 of the sheath 5. In the present embodiment, the first grasp member 71 and the hard portion 6 are integrally molded.

The second grasp member 72 is coupled to the hard portion 6 so as to be capable of performing an opening-closing operation with respect to the first grasp member 71. A penetration hole 78 is formed in the second grasp member 72. A penetration hole 79 is formed in the hard portion 6. A coupling shaft 77 is inserted into the penetration holes 78, and 79, thereby the second grasp member 72 is turnably coupled to the hard portion 6. The second grasp member 72 is turnable about a longitudinal axis Y2 of the coupling shaft 77.

The first grasp member 71 has a first protrusion portion 711 and a second protrusion portion 712. The first protrusion portion 711 and the second protrusion portion 712 are provided in the distal end portion of the first grasp member 71 and protrude in a direction intersecting the longitudinal axis (center axis) Y1. The first protrusion portion 711 and the second protrusion portion 712 are provided as a pair with the longitudinal axis Y1 of the sheath 5 interposed therebetween, and a distal end portion of the second grasp member 72 is positioned between the first protrusion portion 711 and the second protrusion portion 712 in a state in which the first grasp member 71 and the second grasp member 72 are closed.

The link mechanism 76 is constituted of a first link member 76*a*, a first joint member 76*b*, a second link member 76*c*, and a second joint member 76*d*. The first link member 76*a* is coupled to the second link member 76*c* by the first joint member 76*b*. The second link member 76*c* is coupled to the second grasp member 72 by the second joint member 76*d*.

Figure 9:
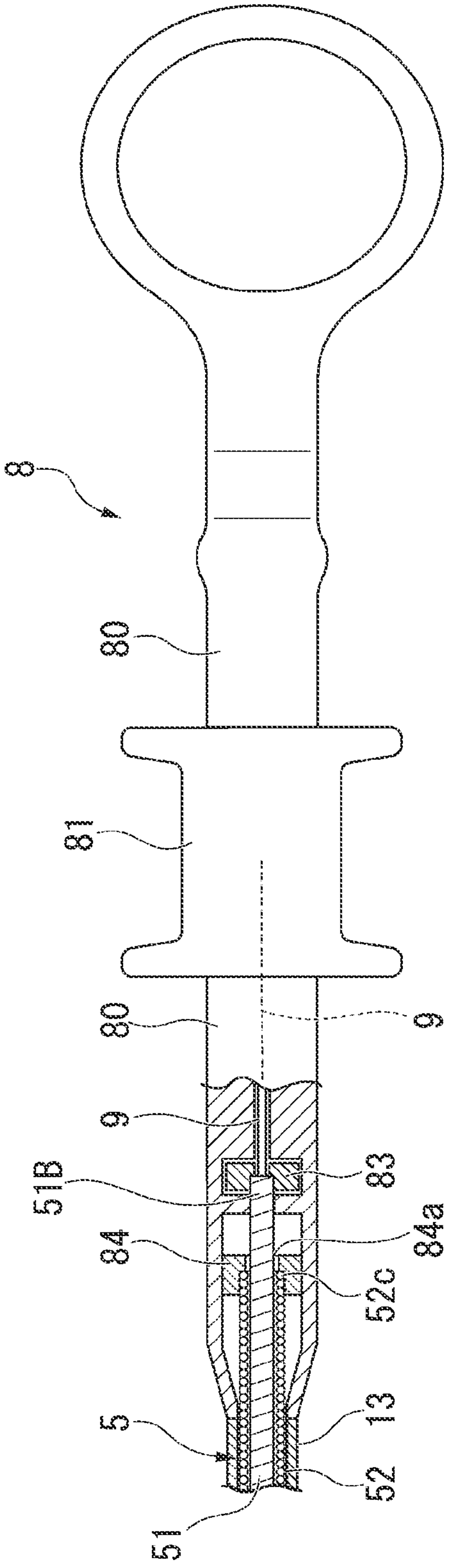
FIG. 9 is a view illustrating a connection part between the sheath and an operation portion in the traction tool in a cross-sectional view.

FIG. 9 is a view illustrating a connection part between the sheath 5 and the operation portion 8 in a cross-sectional view.

The operation portion (handle) 8 has an operation portion main body 80, a first slider 81, a lock member (disk) 83, and a sliding member (key) 84.

A proximal end of the coupling member 13 is fixed to a distal end of the operation portion main body 80. A distal end of the coupling member 13 is fixed to the proximal end portion 1*b* of the proximal shaft 1. For this reason, a relative positional relationship between the proximal shaft 1 and the needle holder 150 is constant.

A proximal end 52C of the second coil sheath 52 is fixed to the sliding member 84 inside the operation portion main body 80. A proximal end 51B of the first coil sheath 51 extending from the second coil sheath 52 is fixed to the lock member 83.

The first slider 81 is coupled to the operation portion main body 80 such that the first slider 81 is advanceable and retractable with respect to the operation portion main body 80 and is capable of advancing and retracting in the axial direction of the operation portion main body 80. The operation wire 9 extending from the first coil sheath 51 is connected to the first slider 81 through the inside of the operation portion main body 80.

The lock member (disk) 83 is formed to have substantially a cylindrical shape. The proximal end 51B of the first coil sheath 51 is fixed to the lock member 83. The lock member 83 and the proximal end 51B are attached such that the lock member 83 and the proximal end 51B is rotatable with respect to the operation portion main body 80 about the axis and is immovable relative to the operation portion main body 80 in the axial direction.

The sliding member (key) 84 is a member sliding inside the operation portion main body 80 in the longitudinal direction and has a penetration hole 84*a* through which the first coil sheath 51 is inserted. The sliding member 84 and the proximal end 52C of the second coil sheath 52 fixed to the sliding member 84 are attached so as to be unrotatable about the axis with respect to the operation portion main body 80 and so as to be movable in the axial direction with respect to the operation portion main body 80 and the first coil sheath 51.

If the operation portion main body 80 is rotated about the axis, the sliding member 84 and the second coil sheath 52 also rotate about the axis together with the operation portion main body 80.

The operation wire 9 is disposed along the longitudinal axis Y1 of the sheath 5 inside the sheath 5. The operation wire 9 is a flexible wire, and is capable of transmitting the amount of operation force from the first slider 81.

As illustrated in FIG. 7, a distal end of the operation wire 9 is fixed to the first link member 76*a* of the link mechanism 76. The proximal end of the operation wire 9 is connected to the first slider 81 of the operation portion 8. That is, the distal end of the operation wire 9 and the second grasp member 72 are connected to each other via the link mechanism 76. The amount of operation force for operating an opening/closing operation of the second grasp member 72 with respect to the first grasp member 71 is transmitted from the first slider 81 to the second grasp member 72 via the operation wire 9 and the link mechanism 76.

Due to advancing and retracting of the first slider 81 with respect to the operation portion main body 80, the operation wire 9 is capable of being made to advance and retract along the longitudinal axis Y1 of the sheath 5 and the grasper 7 is capable of being made to open and close. For example, the operation wire 9 is capable of being pulled toward the operation portion 8 side by moving the first slider 81 toward the proximal end side with respect to the operation portion main body 80.

When the operation wire 9 is pulled toward the operation portion 8 side, the second grasp member 72 moves in a direction to be closed with respect to the first grasp member 71. On the other hand, when the operation wire 9 is pushed out toward the grasper 7 side, the second grasp member 72 moves in a direction to be opened with respect to the first grasp member 71.

[Method for Using Treatment System 300]

Next, with reference to FIGS. 11 to 17, a procedure of using the treatment system 300 of the present embodiment (method for using the treatment system 300) will be described. Specifically, a procedure of suturing a wound W formed in a lumen wall inside a hollow organ such as the digestive tract using the traction tool 100 will be described. FIGS. 11 to 17 are views illustrating a method for using the traction tool 100.

Figure 10:
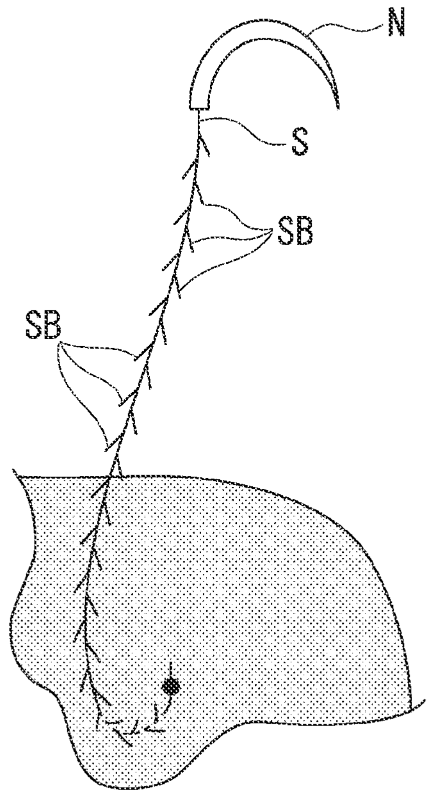
FIG. 10 is a view illustrating a suture thread.

FIG. 10 is a view illustrating a suture thread S.

The suture thread S used in the procedure described below has a plurality of barbs SB disposed side by side along the longitudinal axis. The suture thread S is allowed to move in only a direction in which a suture needle N is attached in a state in which the suture thread S is inserted into a biological tissue. Since the plurality of barbs SB are locked with the biological tissue, the suture thread S is immovable in the opposite direction. In the diagrams except for FIG. 10, illustration of the barbs SB of the suture thread S is omitted.

An operator causes the grasper 7 of the traction tool 100 to protrude from the distal end opening portion 206*a* of the channel 206 of the flexible endoscope 200 before the flexible endoscope 200 is inserted into a hollow organ. The operator grasps the suture needle N with the grasper 7 by retracting the first slider 81. In place of the suture needle N, the suture thread S attached to the suture needle N may be grasped with the grasper 7.

The operator inserts the flexible endoscope 200 into a hollow organ through a natural opening of a patient. The suture needle N or the suture thread S is introduced into a hollow organ in a state of being grasped by the grasper 7 which has protruded through the distal end opening portion 206*a*.

When the suture needle N is grasped by the grasper 7 in an undesired state in direction or a position, the operator temporarily places the suture needle N on the lumen wall and regrasps the suture needle N with the grasper 7. If the suture thread S is grasped when the suture needle N is introduced into the digestive tract, the suture needle N is also temporarily placed on the lumen wall, and the suture needle N is regrasped by the grasper 7. The operator grasps the suture needle N with the grasper 7 by moving the first slider 81 toward the proximal end side along the operation portion main body 80.

[First Step]

Figure 11:
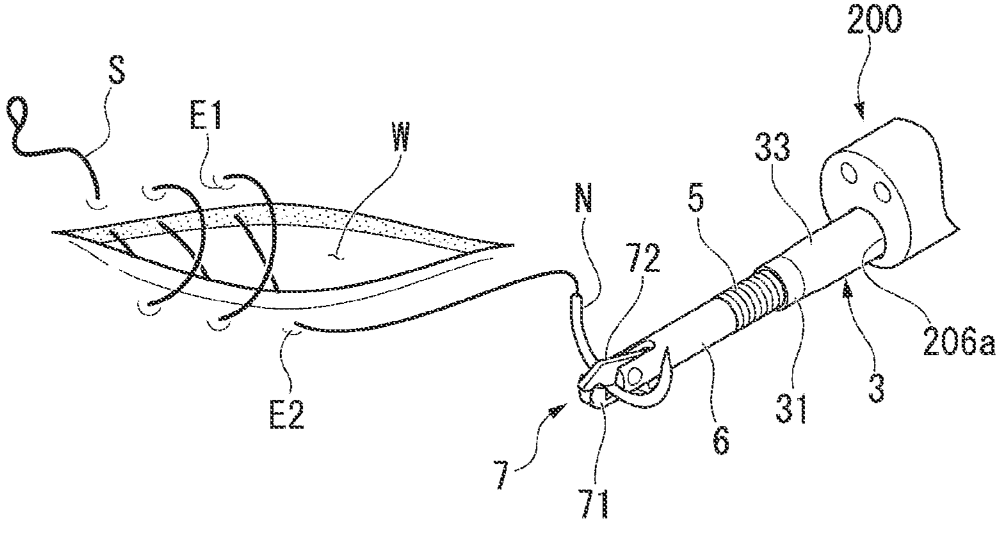
FIG. 11 is a view for explaining a first step and a second step of a procedure of using the traction tool.

FIG. 11 is a view for explaining of a first step and a second step.

In the first step, the operator grasps the suture needle N with the grasper 7 caused to protrude from the distal end opening portion 206*a*, and hooks the suture thread S to a first edge portion E1 by puncturing the suture needle N into the first edge portion E1 of the wound W formed in the lumen wall inside a hollow organ.

[Second Step]

In the second step, the operator grasps the suture needle N with the grasper 7, and hooks the first edge portion E1 extending from the suture thread S to a second edge portion E2 by puncturing the suture needle N into the second edge portion E2 of the wound W formed in the lumen wall inside the digestive tract. The second edge portion E2 is an edge portion of the wound W and is at a position facing the first edge portion E1 with the wound W interposed therebetween.

The operator repeatedly performs the first step and the second step a plurality of times in accordance with the size of the wound W. The wound W illustrated in FIG. 11 indicates a state in which the first step and the second step have been performed three times.

[Third Step]

Figure 12:
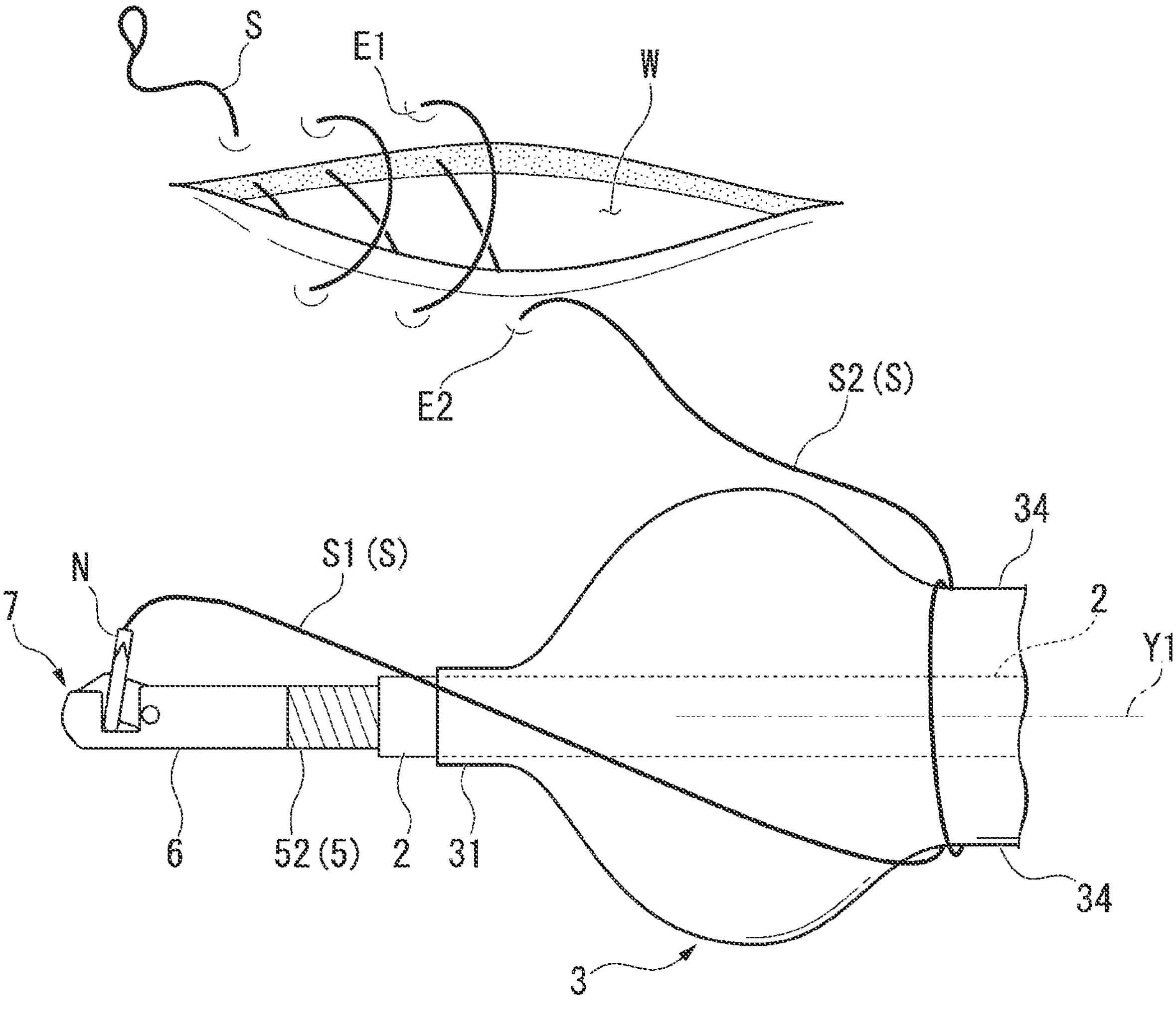
FIG. 12 is a view for explaining a third step of the procedure of using the traction tool.
Figure 13:
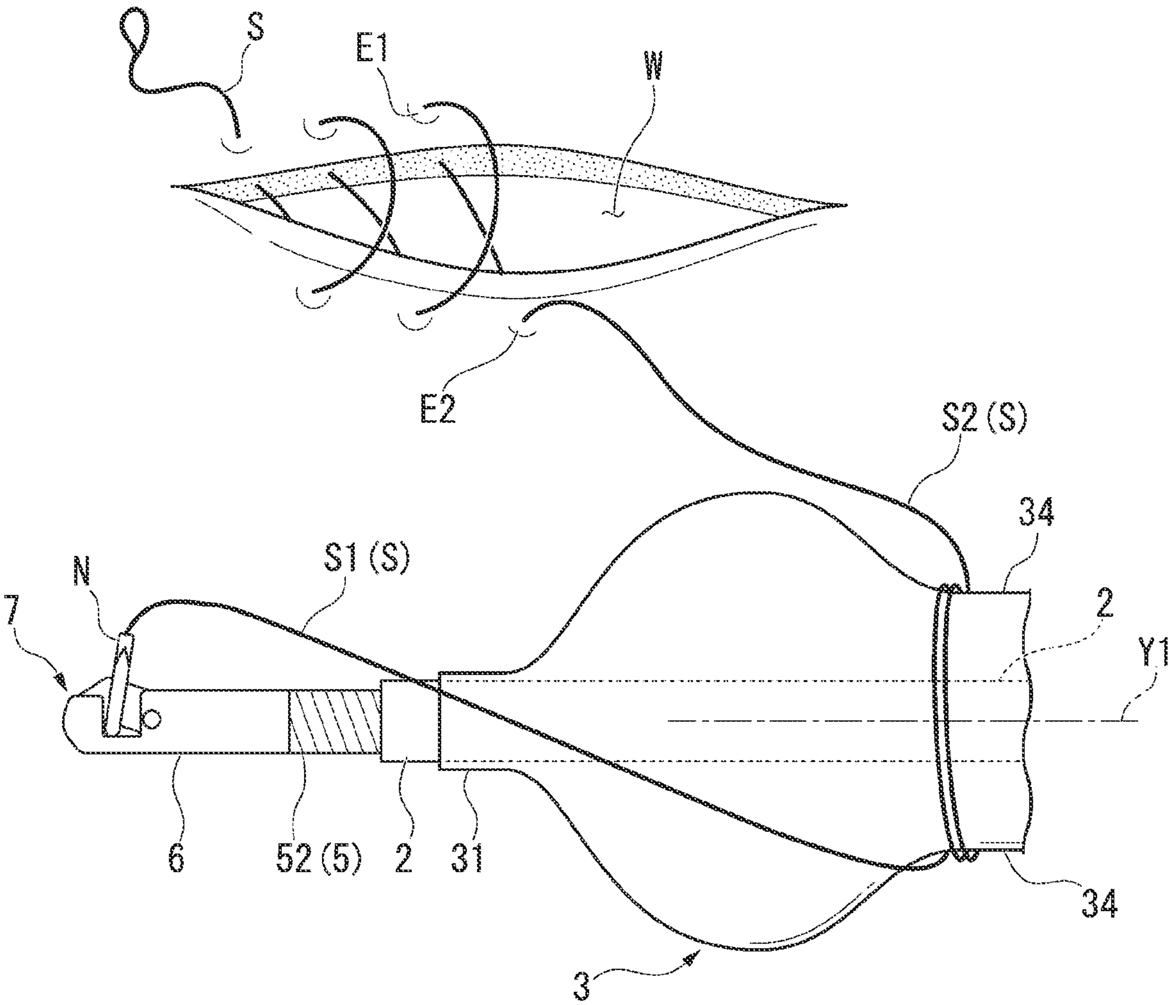
FIG. 13 is another view for explaining the third step of the procedure of using the traction tool.

FIGS. 12 and 13 are views for explaining of a third step.

Before the third step, the operator supplies a fluid from the fluid supply device to the internal space I of the balloon 3 by operating the hub 4. As a result, the balloon 3 is in the diameter-expanded state.

In the third step, the operator holds the suture needle N or a first portion S1 of the suture thread S extending from the second edge portion E2 with the grasp portion (first holder) 7, and winds a second portion S2, which extends between the suture needle N or the first portion S1 and the second edge portion E2, of the suture thread S around the distal shaft 2 while hooking it to the balloon (second holder) 3. The operator rotates the second coil sheath 52 by rotating the operation portion main body 80 about the axis. As a result, the hard portion 6 and the grasper 7 rotate about the longitudinal axis Y1 of the sheath 5. Since the distal shaft 2 is connected to the operation portion main body 80 via the proximal shaft 1 and the coupling member 13, the distal shaft 2 rotates about the longitudinal axis Y1 of the sheath 5 together with the hard portion 6 and the grasper 7.

As illustrated in FIGS. 12 and 13, the second portion S2 of the suture thread S is wound around the distal shaft 2 while being hooked to the balloon (second holder) 3 by rotating the grasper 7 about the longitudinal axis Y1 of the sheath 5. The operator can suitably wind the suture thread S to the distal shaft 2 by hooking the second portion S2 of the suture thread S to the recessed portion 34 of the balloon 3.

[Fourth Step]

Figure 14:
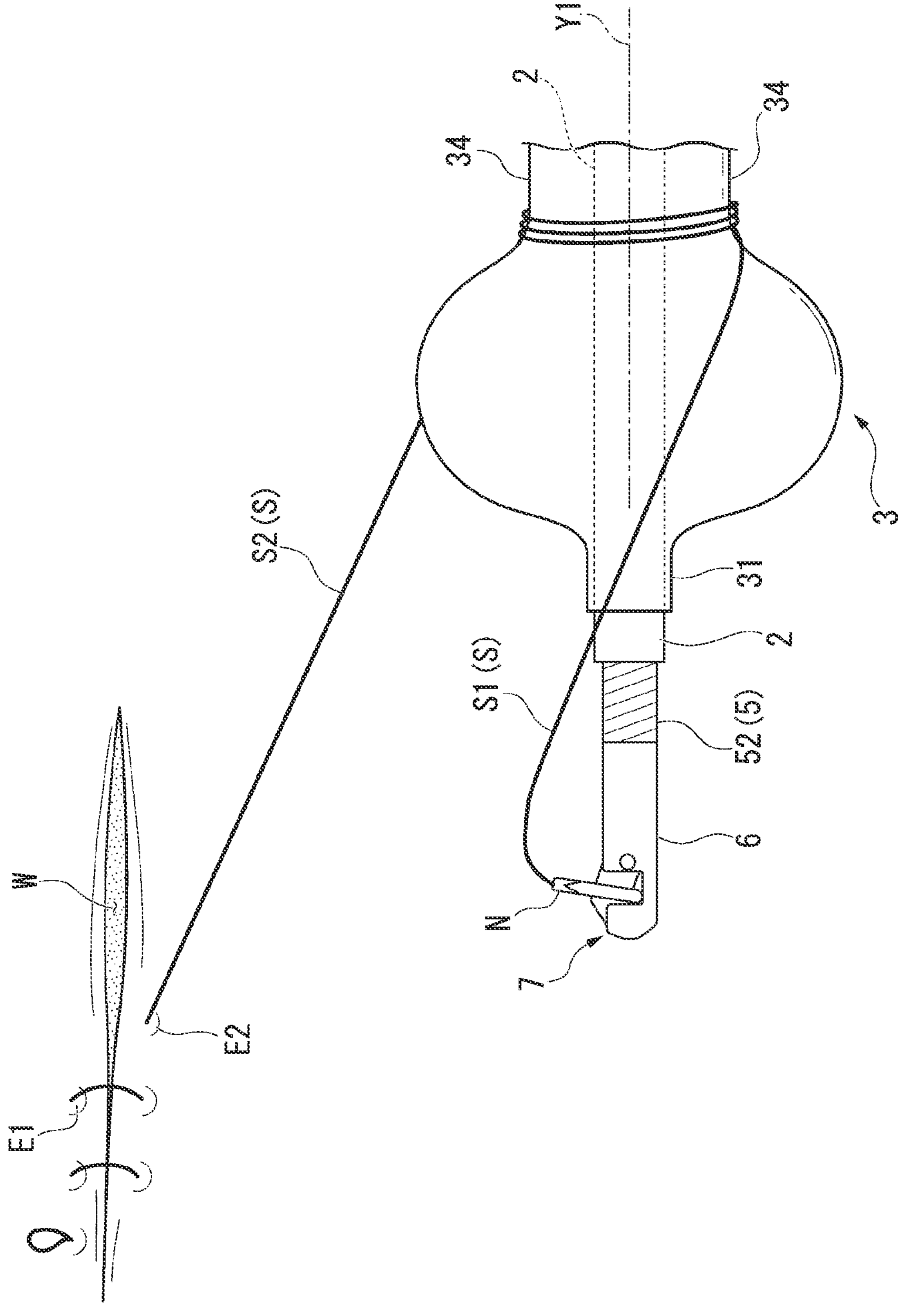
FIG. 14 is a view for explaining a fourth step of the procedure of using the traction tool.

FIG. 14 is a view for explaining of a fourth step.

In the fourth step, the operator performs traction of the suture thread S by retracting the traction tool 100 along the longitudinal axis Y1 of the sheath 5. Specifically, the operator moves the traction tool 100 toward the proximal end side with respect to the flexible endoscope 200. The balloon (second holder) 3 in which suture thread S is hooked moves in a direction away from the second edge portion E2. As a result, a tension is applied to the suture thread S, and the first edge portion E1 and the second edge portion E2 are tightened. In the fourth step, the operator may move the balloon (second holder) 3 in a direction away from the second edge portion E2 by advancing the traction tool 100 along the longitudinal axis Y1 of the sheath 5.

The operator advances the traction tool 100, which has been retracted. As a result, the tension applied to the suture thread S is canceled. Since the suture thread S has the plurality of barbs SB, the tightened state of the first edge portion E1 and the second edge portion E2 is maintained.

FIGS. 15 to 18 are views for explaining of a fifth step.

Figure 15:
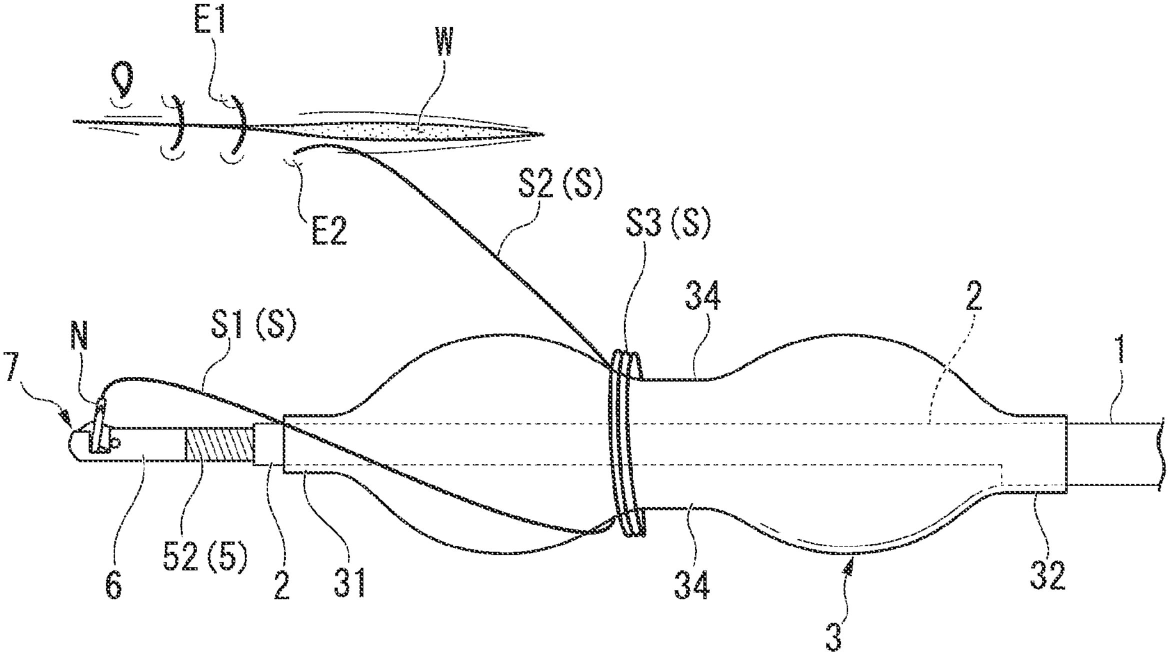
FIG. 15 is a view for explaining a fifth step of the procedure of using the traction tool.
Figure 16:
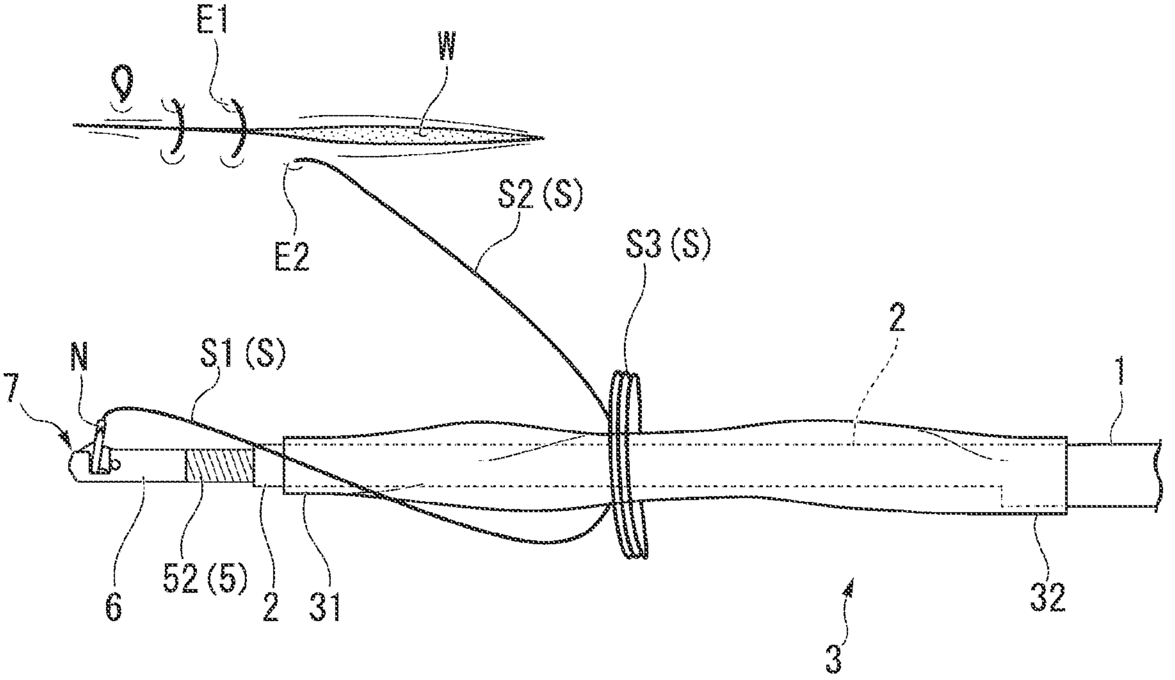
FIG. 16 is another view for explaining the fifth step of the procedure of using the traction tool.

Before the fifth step, the operator discharges a fluid from the stop cock 41 to the fluid supply device by operating the stop cock 41 of the hub 4. As a result, as illustrated in FIGS. 15 and 16, the fluid is discharged from the internal space I, and the balloon 3 returns to the natural state.

Figure 17:
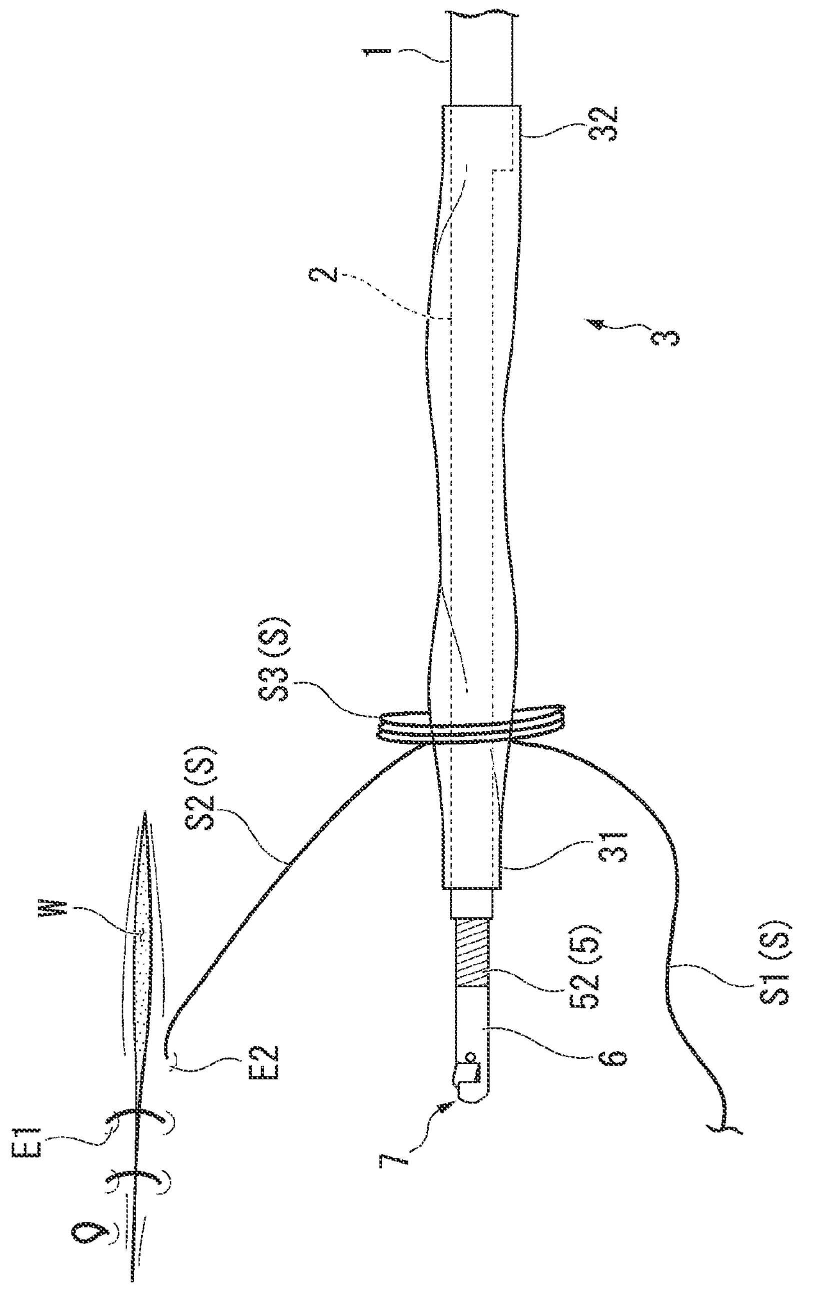
FIG. 17 is another view for explaining the fifth step of the procedure of using the traction tool.
Figure 18:
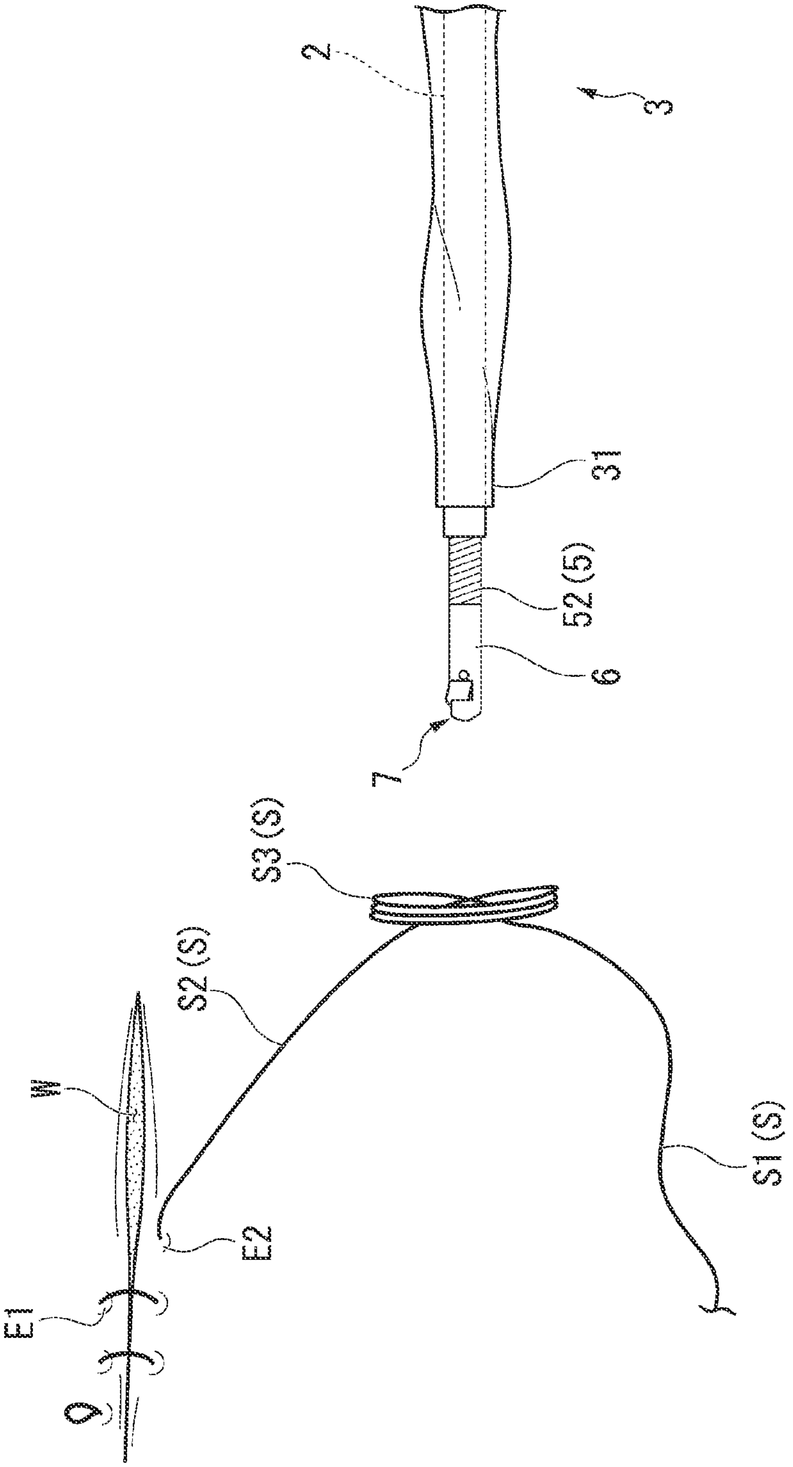
FIG. 18 is another view for explaining the fifth step of the procedure of using the traction tool.

In the fifth step, the operator opens the first grasp member 71 and the second grasp member 72 and separates the first portion S1 of the suture thread S or the suture needle N therefrom. As illustrated in FIGS. 17 and 18, the operator retracts the grasper 7 along the longitudinal axis Y1 of the sheath 5, so that the grasper 7 passes through the inside of a loop S3 of the suture thread S formed by being wound around the distal shaft 2. When the first step is performed again, the operator grasps the suture needle N with the grasper 7.

The operator sutures the wound W which has not sutured by repeatedly performing the first step to the fifth step a plurality of times in accordance with the size of the wound W. The operator cuts the suture thread S, takes the cut suture thread S and the suture needle N out of the body, and ends the procedure.

According to the traction tool 100 and the procedure using the traction tool 100 (method of use) according to the present embodiment, for example, in suturing work inside a confined hollow organ such as the stomach, a wound can be sufficiently stitched by performing traction by winding the suture thread S attached to the suture needle N around the distal shaft 2.

According to the traction tool 100 and the procedure using the traction tool 100 (method of use) according to the present embodiment, since the suture thread S is wound around the balloon 3 which has expanded in diameter, the amount of pulling the suture thread S can be increased compared to a case that the suture thread S is directly wound around the distal shaft 2.

Hereinabove, the first embodiment of the present disclosure has been described with reference to the drawings, but specific constitutions are not limited to this embodiment, and design change and the like within a range not departing from the gist of the present disclosure are also included therein. In addition, the constituent elements illustrated in the embodiment and the modified examples described above can be constituted to be suitably combined.

Modified Example 1

Figure 19:
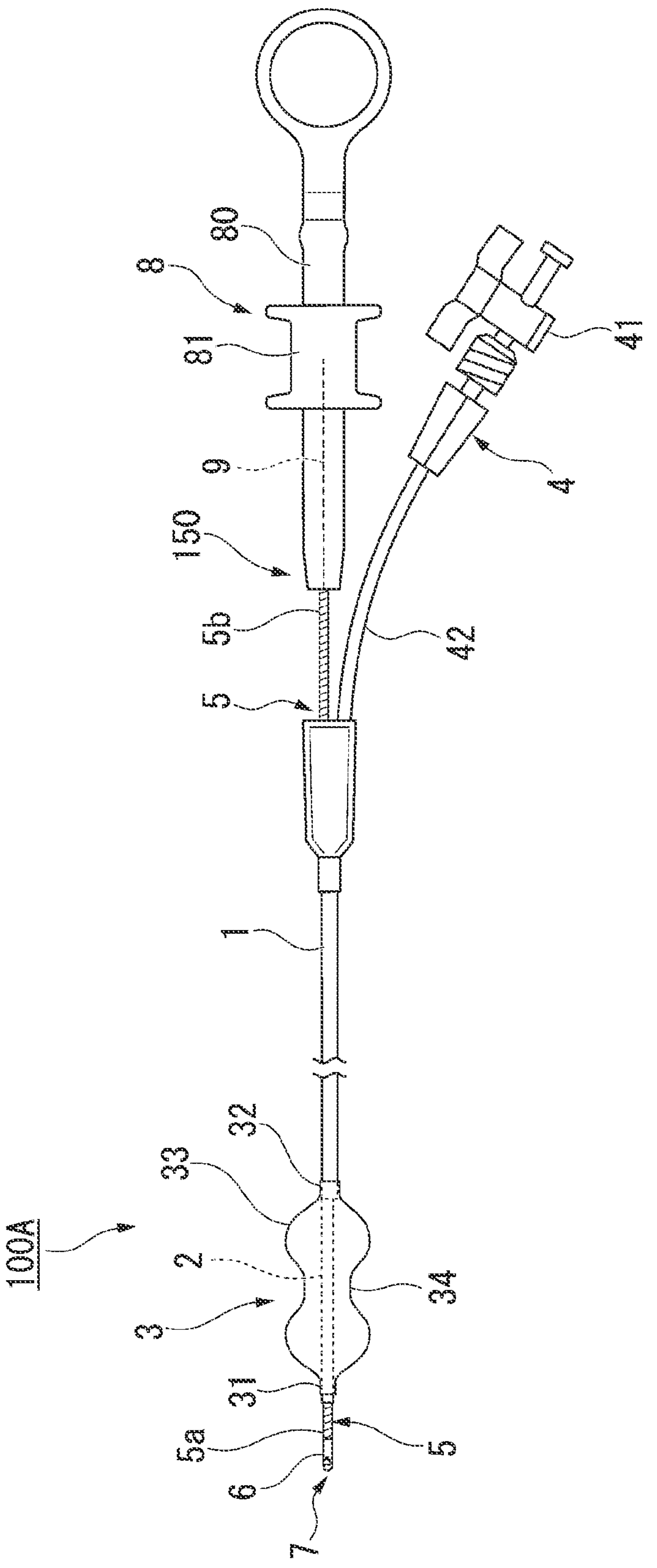
FIG. 19 is a general view of a modified example of the traction tool.

In the foregoing embodiment, the operation portion main body 80 and the proximal shaft 1 are coupled to each other by the coupling member 13. However, the aspect of the traction tool 10 is not limited to this. FIG. 19 is a general view of a traction tool 100A that is a modified example of the traction tool 100. The traction tool 100A does not have the coupling member 13. Accordingly, even when the operator rotates the operation portion main body 80 about the axis, the proximal shaft 1 and the distal shaft 2 do not rotate. On the other hand, the sheath 5 and the grasper 7, which have been coupled to the operation portion main body 80 so as to be unrotatable by the sliding member 84, rotate when the operator rotates the operation portion main body 80.

The operator can rotate the sheath 5 and the grasper 7 while restraining the balloon 3 attached to the proximal shaft 1 and the distal shaft 2 from rotating by rotating the operation portion main body 80 about the axis.

Modified Example 2

Figure 20:
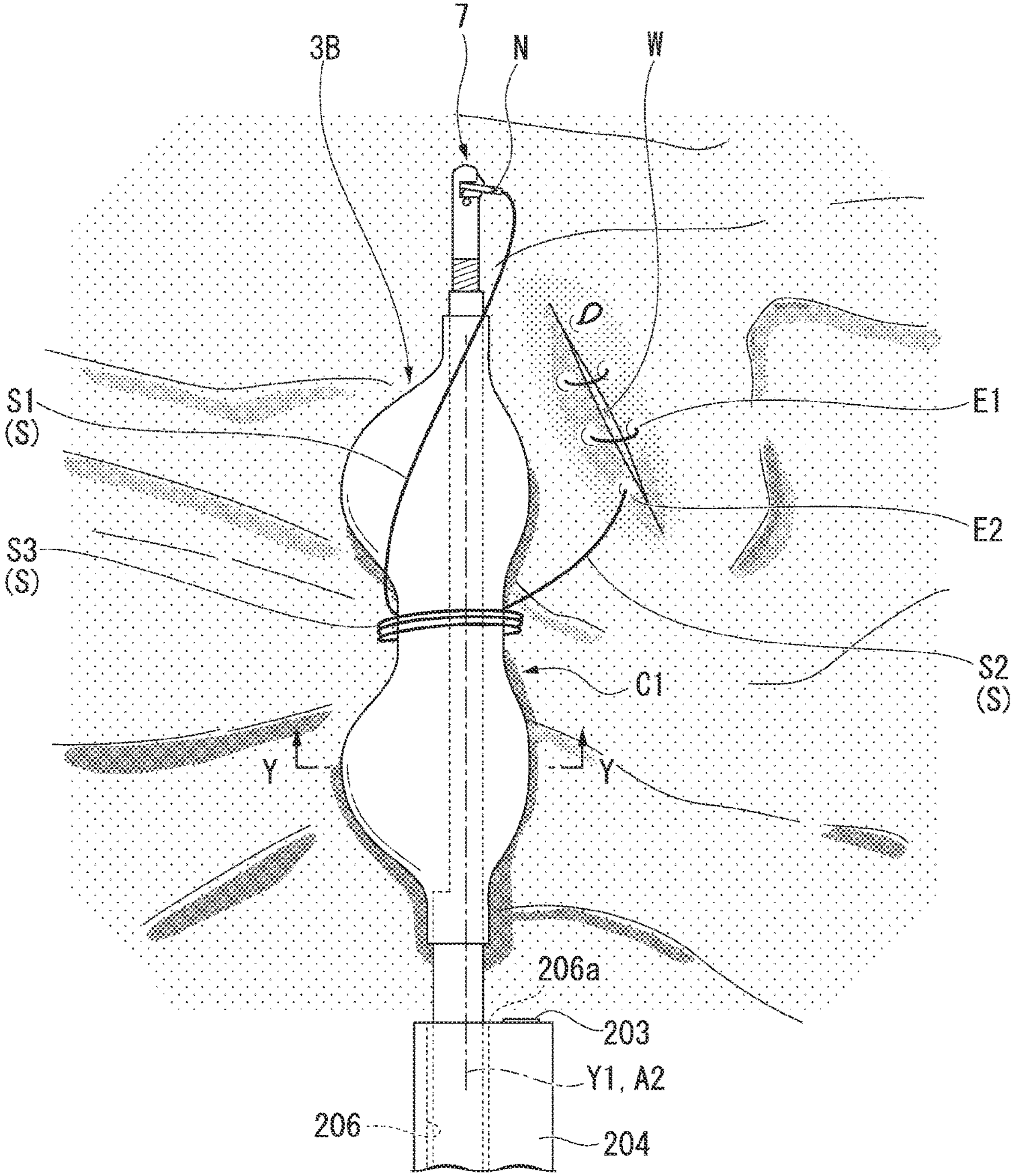
FIG. 20 is a view illustrating a usage aspect of a modified example of the balloon.
Figure 21:
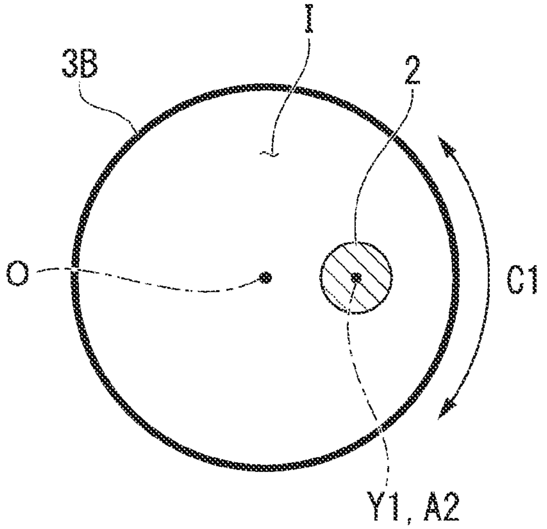
FIG. 21 is a cross-sectional view along line Y-Y in FIG. 20.

In the foregoing embodiment, as illustrated in FIG. 3, a center axis A1 of the distal shaft 2 coincides with a center axis O of the balloon 3 in the longitudinal direction. However, the form of the balloon 3 is not limited to this. FIG. 20 is a view illustrating a usage aspect of a balloon 3B that is a modified example of the balloon 3. FIG. 21 is a cross-sectional view along line Y-Y in FIG. 20. A center axis A2 of the distal shaft 2 is eccentric from the center axis O of the balloon 3B. For this reason, a first outer circumferential portion C1 in which the distance from the distal shaft 2 to the outer circumferential portion of the balloon 3B is shorter than those of other parts is formed. As illustrated in FIG. 20, the operator is easy to observe the wound W via the image capturing portion 203 of the endoscope 200 by arranging the first outer circumferential portion C1 directed to the wound W.

Modified Example 3

Figure 22:
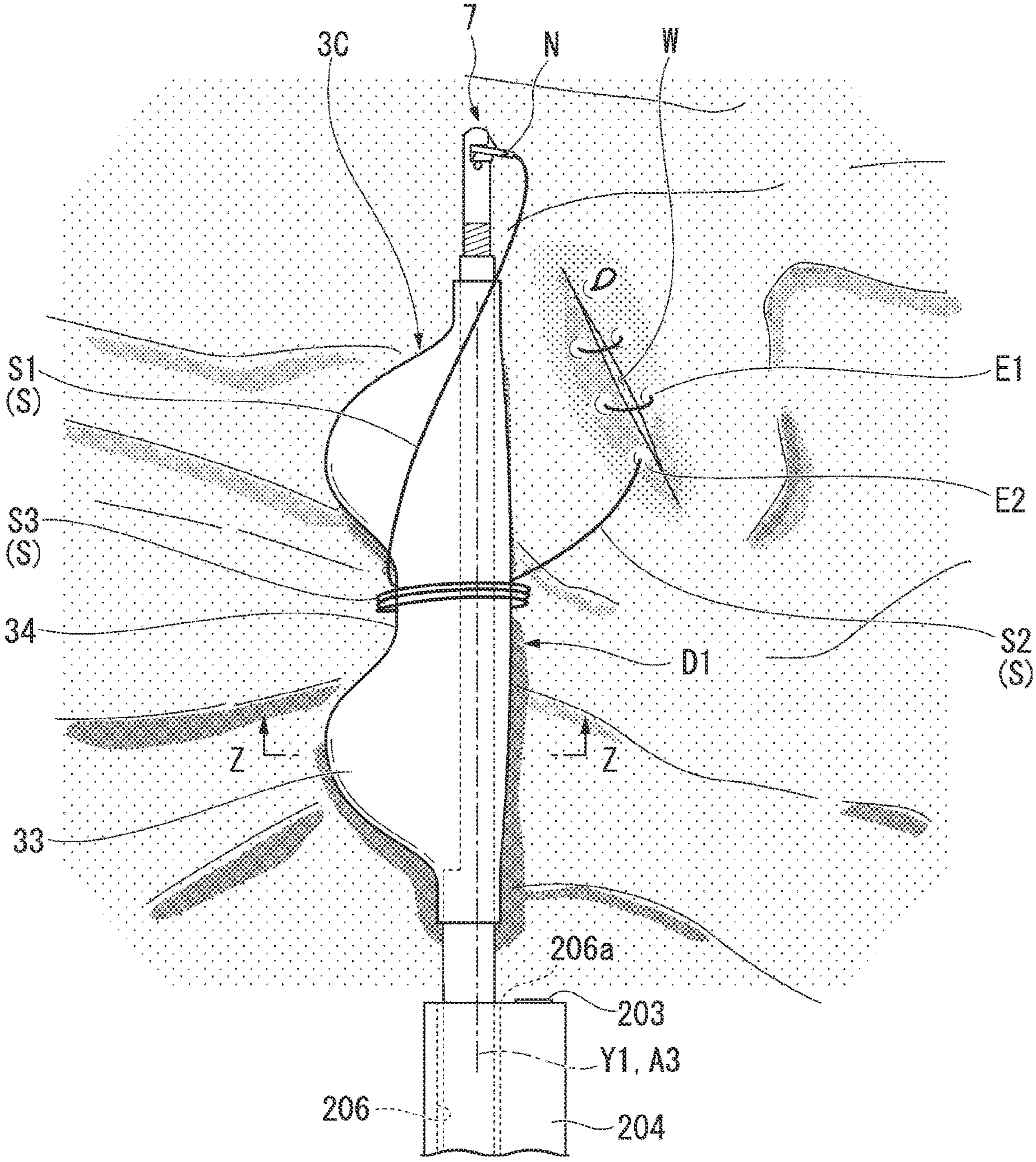
FIG. 22 is a view illustrating a usage aspect of another modified example of the balloon.
Figure 23:
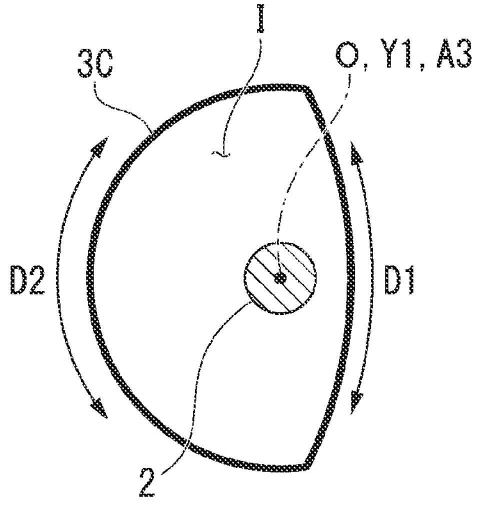
FIG. 23 is a cross-sectional view along line Z-Z in FIG. 22.

FIG. 22 is a view illustrating a usage aspect of a balloon 3C that is another modified example of the balloon 3. FIG. 23 is a cross-sectional view along line Z-Z in FIG. 22. A center axis A3 of the distal shaft 2 substantially coincides with the center axis O of the balloon 3C. As illustrated in FIG. 23, the balloon 3C is asymmetrically expanded in diameter with respect to the center axis O of the balloon 3C. As illustrated in FIG. 23, the outer circumferential portion of the balloon 3C has a first diameter-expanded portion D1 and a second diameter-expanded portion D2. In the balloon 3C in the diameter-expanded state, the distance from the distal shaft 2 to the first diameter-expanded portion D1 is shorter than the distance from the distal shaft 2 to the second diameter-expanded portion D2. As illustrated in FIG. 22, it is easy for the operator to observe the wound W via the image capturing portion 203 of the endoscope 200 by arranging the first diameter-expanded portion D1 directed to the wound W.

Modified Example 4

Figure 24:
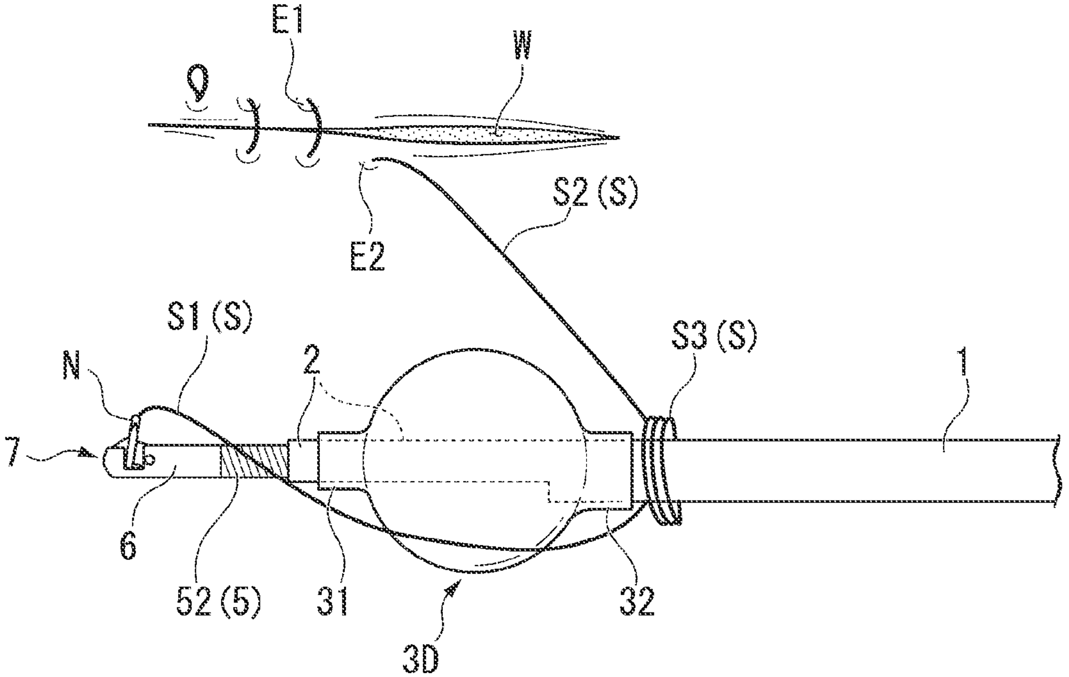
FIG. 24 is a view illustrating a modified example of the balloon.

In the foregoing embodiment, the balloon 3 has the recessed portion 34 formed in the intermediate portion in the longitudinal direction. The operator winds the suture thread S around the distal shaft 2 while hooking it to the recessed portion 34 of the balloon 3 or the like. However, the aspect of the balloon 3 and the method for using the balloon 3 are not limited to these. FIG. 24 is a view illustrating a balloon 3D that is a modified example of the balloon 3. The balloon 3D is formed to have a spherical shape in the diameter-expanded state. The operator directly winds the suture thread S around the proximal shaft 1 while hooking the suture thread S to the entire balloon 3D. The operator can perform a procedure similar to that in the foregoing embodiment using the balloon 3D of which the entire form is simpler than the balloon 3.

Modified Example 5

Figure 25:
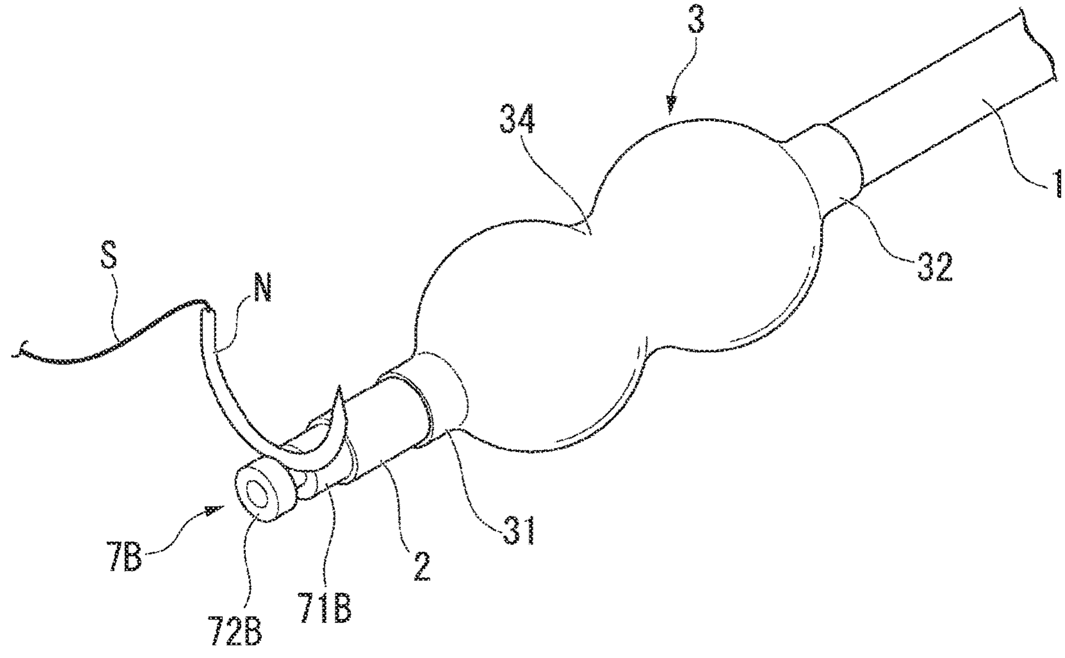
FIG. 25 is a perspective view illustrating a modified example of a grasp portion of the traction tool.

In the foregoing embodiment, the grasper 7 is opened and closed to grasp the suture needle N or the like. However, the form of the grasper 7 is not limited to the example. FIG. 25 is a perspective view illustrating a grasper 7B that is a modified example of the grasper 7. The grasp portion (first holder) 7B has a first grasp member 71B and a second grasp member 72B. The second grasp member 72B is provided closer to the distal end side than the first grasp member 71B. The second grasp member 72B is capable of advancing and retracting with respect to the first grasp member 71B. The grasp portion (first holder) 7B is capable of grasping the suture needle N or the suture thread S by sandwiching the suture needle N or the suture thread S between the first grasp member 71B and the second grasp member 72B.

Modified Example 6

Figure 26:
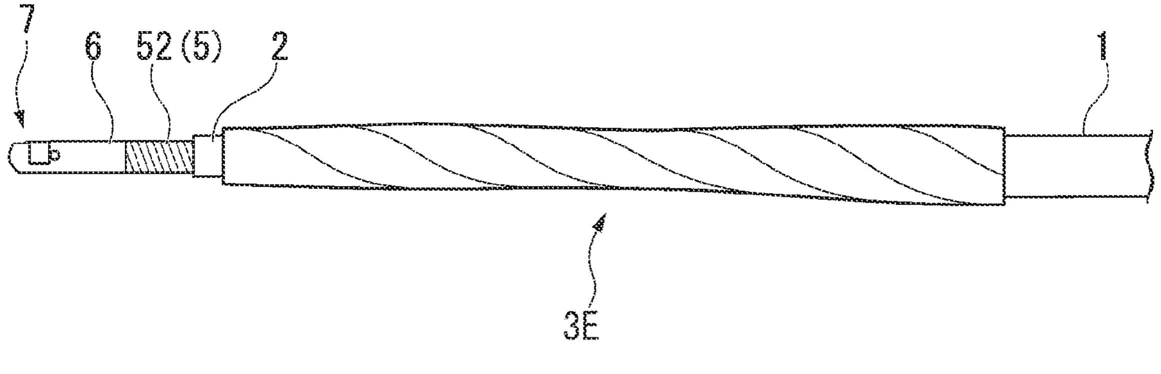
FIG. 26 is a view illustrating another modified example of the balloon.

In the foregoing embodiment, the balloon 3 is a compliant balloon which is expanded and contracted in diameter due to elastic deformation. However, the aspect of the balloon 3 is not limited to this. FIG. 26 is a view illustrating a balloon 3E that is a modified example of the balloon 3. The balloon 3E is a non-compliant balloon which is formed of anon-elastic material such as a nylon. As illustrated in FIG. 26, the balloon 3E is wound around the distal shaft 2 in a folded state. When a fluid is supplied to the internal space I of the balloon 3E, the balloon 3E is in the diameter-expanded state.

Modified Example 7

Figure 27:
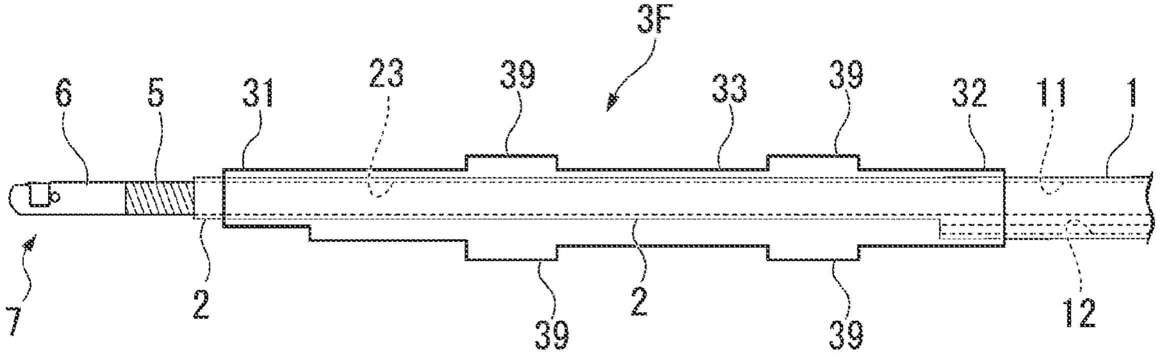
FIG. 27 is a view illustrating another modified example of the balloon.

In the foregoing embodiment, a projection portion to which the suture thread S can be hooked in the natural state is not formed in the balloon 3. However, the aspect of the balloon 3 is not limited to this. FIG. 27 is a view illustrating a balloon 3F that is a modified example of the balloon 3. The balloon 3F has a projection portion 39 to which the suture thread S is capable of being hooked even in the natural state. When the balloon 3F is used, in the third step, it is easy for the operator to wind the second portion S2 of the suture thread S around the distal shaft 2 even before the balloon 3F is expanded in diameter. Therefore, the traction of the suture thread S can be performed without expanding the balloon by winding the suture thread S around the distal shaft 2.

Second Embodiment

A treatment system according to a second embodiment of the present disclosure will be described with reference to FIGS. 28 and 29. In the following description, the same reference signs are applied to constituents common to those which have already been described, and a duplicate description will be omitted.

Figure 28:
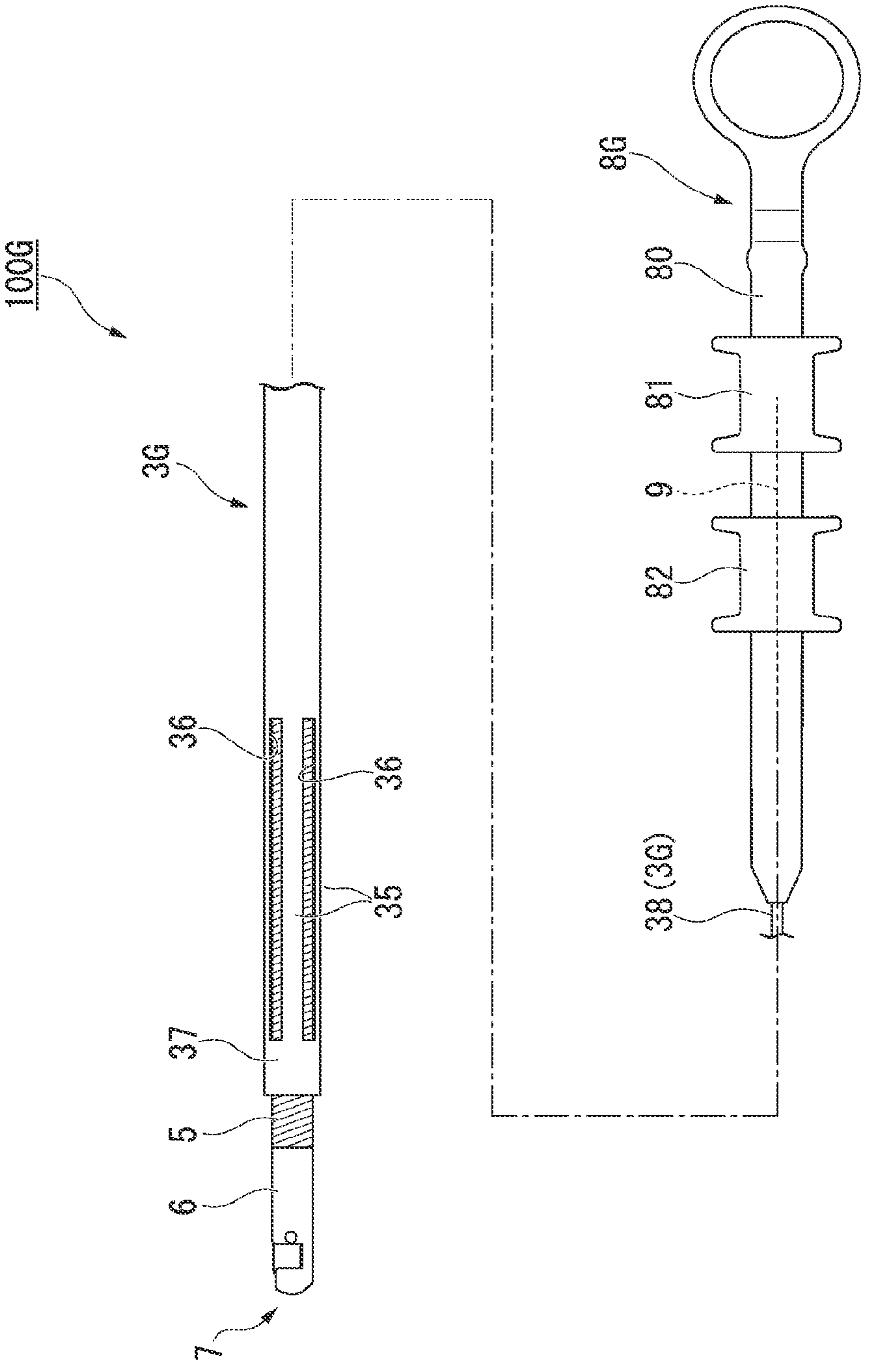
FIG. 28 is a view illustrating a traction tool of a treatment system according to a second embodiment.

FIG. 28 is a view illustrating a traction tool 100G. The treatment system according to the second embodiment includes the flexible endoscope 200 and the traction tool 100G. The traction tool 100G is used by being inserted into the flexible endoscope 200. The traction tool 100G includes a resin sheath 3G, a sheath (shaft) 5, the hard portion 6, the grasp portion (first holder) 7, an operation portion 8G, and the operation wire 9.

The resin sheath 3G is a cylindrical member formed of a resin, and the sheath 5 is inserted therethrough. A distal end portion 37 of the resin sheath 3G is fixed to the distal end 5*a* of the sheath 5 by thermal contraction, an adhesive, or the like. The distal end portion 37 of the resin sheath 3G may be fixed by being bitten between the metal strand wires of the second coil sheath 52 at the distal end 5*a* of the sheath 5. A proximal end portion 38 of the resin sheath 3G is attached to the operation portion 8G so as to be advanceable and retractable.

The resin sheath 3G has a diameter-expanded portion 35 closer to the proximal end side than the distal end portion 37. The diameter-expanded portion (second holder) 35 is formed by providing four slits 36 in the resin sheath 3G. The four slits 36 extend in the longitudinal direction of the resin sheath 3G and are arranged in a circumferential direction of the resin sheath 3G at an equal interval. The diameter-expanded portion 35 is a belt-shaped member interposed between the slits 36 adjacent to each other in the circumferential direction. The number of slits 36 is not limited to four.

The operation portion 8G has the operation portion main body 80, the first slider 81, a second slider 82, the lock member (disk) 83, and the sliding member (key) 84.

The second slider 82 is coupled so as to be advanceable and retractable with respect to the operation portion main body 80. The second slider 82 is advanceable and retractable in the axial direction of the operation portion main body 80. The proximal end portion 38 of the resin sheath 3G is connected to the second slider 82 through the inside of the operation portion main body 80.

Figure 29:
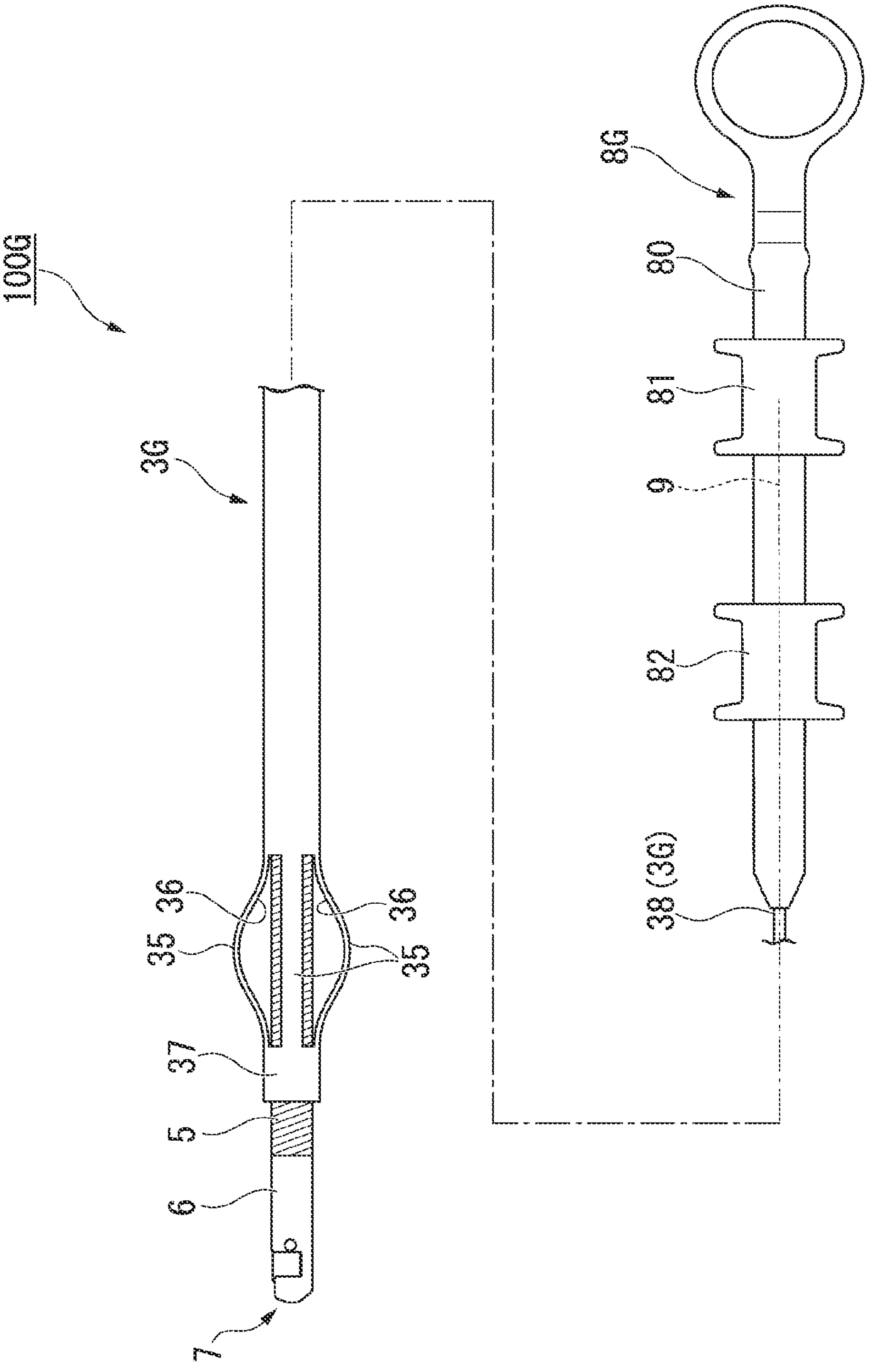
FIG. 29 is a view illustrating the traction tool in which a diameter-expanded portion is expanded in diameter.

FIG. 29 is a view illustrating the traction tool 100G in which the diameter-expanded portion 35 is expanded in diameter. The operator advances the resin sheath 3G with respect to the sheath 5 by moving the second slider 82 toward the distal end side along the operation portion main body 80. As a result, as illustrated in FIG. 29, the diameter-expanded portion 35 bents outside in the radial direction and expands (increased in diameter) in the radial direction. When the operator returns the second slider 82 to the proximal end side along the operation portion main body 80, the diameter-expanded portion 35 returns to the original shape. The operator can expand and contract the diameter of the diameter-expanded portion 35 by advancing and retracting the second slider 82.

Similar to the traction tool 100 of the first embodiment, the operator can perform a procedure of performing traction of the suture thread S using the traction tool 100G. In the third step, the operator holds the suture needle N or the first portion S1 of the suture thread S extending from the second edge portion E2 with the grasp portion (first holder) 7, and winds the second portion S2, which extends between the suture needle N or the first portion S1 and the second edge portion E2, of the suture thread S around the sheath (shaft) 5 while hooking the second portion S2 to the diameter-expanded portion 35 expanded in diameter. In the fourth step, the operator performs traction of the suture thread S by retracting the traction tool 100G along the longitudinal axis Y1 of the sheath 5.

According to the traction tool 100G and the procedure using the traction tool 100G (method of use) according to the present embodiment, for example, in suturing work inside a confined hollow organ such as the stomach, a wound can be sufficiently stitched by winding the suture thread S attached to the suture needle N around the sheath (shaft) 5 and pulling it.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A traction system for performing traction of a suture thread, the traction system comprising:
- a suture needle;
- the suture thread attached to the suture needle;
- a shaft;
- a first holder having a first grasp member and a second grasp member, wherein the first holder is attached to a distal end of the shaft, and the first grasp member and the second grasp member are configured to grasp the suture needle; and
- a second holder positioned closer to a proximal end side of the shaft than the first holder and wherein the second holder is expandable radially outward, wherein the traction system is configured to perform traction of the suture thread by winding the suture thread around the second holder extended in a radial direction in a state in which the suture thread or the suture needle attached to the suture thread is held by the first holder.

2. The traction system according to claim 1, wherein the second holder is a balloon which is bonded to an outer circumferential surface of the shaft.

3. The traction system according to claim 2, wherein a center axis of the shaft is eccentric from a center axis of the balloon.

4. The traction system according to claim 2, wherein a center axis of the shaft coincides with a center axis of the balloon, and wherein the balloon is asymmetrically expanded in diameter with respect to the center axis of the balloon.

5. The traction system according to claim 1, wherein the second holder is a diameter-expanded portion formed in a resin sheath through which the shaft is inserted, wherein a distal end portion of the resin sheath is fixed to the shaft, and wherein the diameter-expanded portion is expanded in diameter by moving a proximal end portion of the resin sheath toward a distal side.

6. The traction system according to claim 1, wherein the second holder is expandable in a radial direction of the shaft in a state that the first grasp member and second grasp member grasp the suture needle.

7. The traction system according to claim 1,
wherein the second holder is expandable in a radial direction of the shaft in a state that the suture thread attached to the suture needle is located on the second holder.

8. The traction system according to claim 1,
wherein the second holder is expandable in a radial direction of the shaft in a state that the first grasp member and the second grasp member grasping the suture needle and the suture thread attached to the suture needle are located on the second holder.

9. The traction system according to claim 1,
wherein the first grasp member is configured to open and close with respect to the second grasp member.

10. A traction system for a suture thread, the traction system comprising:
a suture needle;
the suture thread attached to the suture needle;
a shaft;
a first holder having a first grasp member and a second grasp member, wherein the first holder is attached to a distal end of the shaft, and the first grasp member and the second grasp member are configured to grasp the suture needle; and
a second holder positioned closer to a proximal end side of the shaft than the first holder, wherein the second holder is a balloon bonded to an outer circumferential surface of the shaft and is expandable in a radial direction of the shaft in a state that the first grasp member and the second grasp member grasp the suture needle, and wherein the traction system is configured to perform traction of the suture thread by winding the suture thread around the second holder extended in a radial direction in a state in which the suture thread or the suture needle attached to the suture thread is held by the first holder.

11. A suturing method for closing a wound formed in a lumen wall of a hollow organ using a traction tool including:
a shaft;
a first holder, the first holder including a first grasp member and a second grasp member, wherein the first holder is attached to a distal end of the shaft, and wherein the first grasp member and the second grasp member are configured to grasp a suture needle; and
a second holder which is configured to be expandable in a radial direction of the shaft, the suturing method comprising:
passing a suture thread through a first edge portion of the wound;
passing the suture thread through a second edge portion of the wound, the suture thread extending from the first edge portion, and the second edge portion being located at a position facing the first edge portion with the wound interposed therebetween;
winding the suture thread around the second holder extending in a radial direction by rotating the second holder around a longitudinal axis of the shaft in a state in which the suture thread is held by the first holder or the suture needle is attached to the suture thread and is held by the first holder; and
moving the second holder away from the wound in a state that the second holder expanded radially is winded by the suture thread so that the wound is closed.

12. The suturing method according to claim 11, wherein passing the suture thread through the first edge portion and the second edge portion is conducted by piercing a suture needle grasped by the first grasp member and the second grasp member.

* * * * *